(12) United States Patent
Wright et al.

(10) Patent No.: US 10,468,140 B2
(45) Date of Patent: Nov. 5, 2019

(54) SYSTEMS, METHODS, AND DEVICES FOR AGGREGATED HEALTH DATA PROCESSING AND TREATMENT RECOMMENDATION GENERATION PLATFORMS

(71) Applicant: Adventia Technology, LLC, Ellendale, TN (US)

(72) Inventors: David Bruce Wright, Bartlett, TN (US); Shannan Michelle Booth Purser, Tega Cay, SC (US); Bryan Ross Winter, Bartlett, TN (US)

(73) Assignee: Adventia Technology, LLC, Ellendale, TN (US)

(*) Notice: Subject to any disclaimer, the term of this patent is extended or adjusted under 35 U.S.C. 154(b) by 0 days.

(21) Appl. No.: 16/167,243

(22) Filed: Oct. 22, 2018

(65) Prior Publication Data
US 2019/0122769 A1 Apr. 25, 2019

Related U.S. Application Data

(60) Provisional application No. 62/576,230, filed on Oct. 24, 2017, provisional application No. 62/576,268, filed on Oct. 24, 2017.

(51) Int. Cl.
*G16H 50/30* (2018.01)
*G16H 15/00* (2018.01)
(Continued)

(52) U.S. Cl.
CPC .......... *G16H 50/30* (2018.01); *G06F 3/0482* (2013.01); *G16H 15/00* (2018.01); *G16H 20/10* (2018.01);
(Continued)

(58) Field of Classification Search
USPC ....................................................... 705/2–4
See application file for complete search history.

(56) References Cited

U.S. PATENT DOCUMENTS 8,543,422 B2 9/2013 Maman et al.
2003/0229284 A1* 12/2003 Stein .................. A61B 5/02007
600/454
(Continued)

FOREIGN PATENT DOCUMENTS

WO WO 2016-065293 A1 4/2016

OTHER PUBLICATIONS

Souza, Nathan M., et al. "Computerized clinical decision support systems for primary preventive care: a decision-maker-researcher partnership systematic review of effects on process of care and patient outcomes." Implementation Science 6.1 (2011): 87.*
(Continued)

*Primary Examiner* — Mark Holcomb
(74) *Attorney, Agent, or Firm* — Knobbe Martens Olson & Bear, LLP

(57) ABSTRACT

Some embodiments described herein are directed to a universal health platform that may efficiently provide sophisticated health data processing and treatment recommendations. In some embodiments, the platform may be configured to allow a user (e.g. a patient or health professional) to input or import a vast and varied collection of data including health, medical, lifestyle, historical, and other relevant data. The platform may be configured to process this data through a multifaceted and dynamically updated decision-making protocol to create a personalized patient report. In some embodiments, the personalized patient report may comprise various medications, treatment, preventative, health, lifestyle, and behavioral recommendations and/or plans. In some embodiments, the data input and personalized patient report features are communicated to a user through a dynamic user interface configured to automatically update and adjust based on newly inputted data or user selection and/or rejection of recommendations in the personalized patient report.

20 Claims, 26 Drawing Sheets

(51) Int. Cl.
  *G16H 20/10* (2018.01)
  *G06F 3/0482* (2013.01)
  *G16H 20/60* (2018.01)
  *G16H 20/30* (2018.01)
  *G16H 20/70* (2018.01)
  *G16H 10/60* (2018.01)
(52) U.S. Cl.
  CPC ............ *G16H 20/30* (2018.01); *G16H 20/60* (2018.01); *G16H 20/70* (2018.01); *G16H 10/60* (2018.01)

(56) References Cited

U.S. PATENT DOCUMENTS

| | | | |
|---|---|---|---|
| 2005/0240444 A1* | 10/2005 | Wooten | G06F 19/3481 705/3 |
| 2007/0239490 A1 | 10/2007 | Sullivan | |
| 2010/0094657 A1 | 4/2010 | Stern et al. | |
| 2011/0077958 A1* | 3/2011 | Breitenstein | G06Q 10/10 705/2 |
| 2014/0074509 A1* | 3/2014 | Amarasingham | G16H 10/60 705/3 |
| 2016/0029972 A1 | 2/2016 | Lenehan et al. | |

OTHER PUBLICATIONS

Written Opinion dated Feb. 11, 2019 for International Application No. PCT/US2018/056917 in 8 pages.
International Search Report dated Feb. 12, 2019 for International Application No. PCT/US2018/056917 in 3 pages.

* cited by examiner

510 → WHAT YOU NEED TO DISCUSS WITH YOUR DOCTOR

512 → YOUR GENERAL CARDIOVASCULAR HEALTH

502 → Ramipril

Discuss the need for a prescription for Ramipril.

508 — In the landmark HOPE trial from 2000, patients at high risk for cardiovascular disease, including those with Metabolic Syndrome, who took Ramipril showed a dramatic 34% decrease in diabetes, 32% decrease in stroke, 20% decrease in heart attack, and a 26% decrease in cardiovascular deaths.

512 → SUPPLEMENTS THAT HELP IMPROVE MULTIPLE RISK FACTORS

The supplements below have been shown to improve risk factors for heart attack, stroke, and/or diabetes. Supplements specific to improving your cholesterol, inflammation, insulin resistance/blood sugar, and/or arteries will be outlined in their respective sections.

508 — Note that for some supplement recommendations, we recommend a specific brand or product line. We do not receive any financial incentive for doing so. The recommended brand or product line is given, because we have found it to be the most effective at achieving the results suggested by research studies.

514 — ⓘ Before beginning any supplements, you must check with your doctor and/or pharmacist as there could be possible interactions with other medical conditions or medications that we are unaware of.

502 → Soluble fiber

Discuss taking Sugar-Free Metamucil or Konsyl with your doctor.

508 — If your doctor approves, we recommend daily taking one rounded teaspoon of Sugar-Free Metamucil or Konsyl (dissolved in 8 ounces of water) before one of your meals. We would then recommend gradually working up to daily taking a rounded teaspoon 3 times a day before meals.

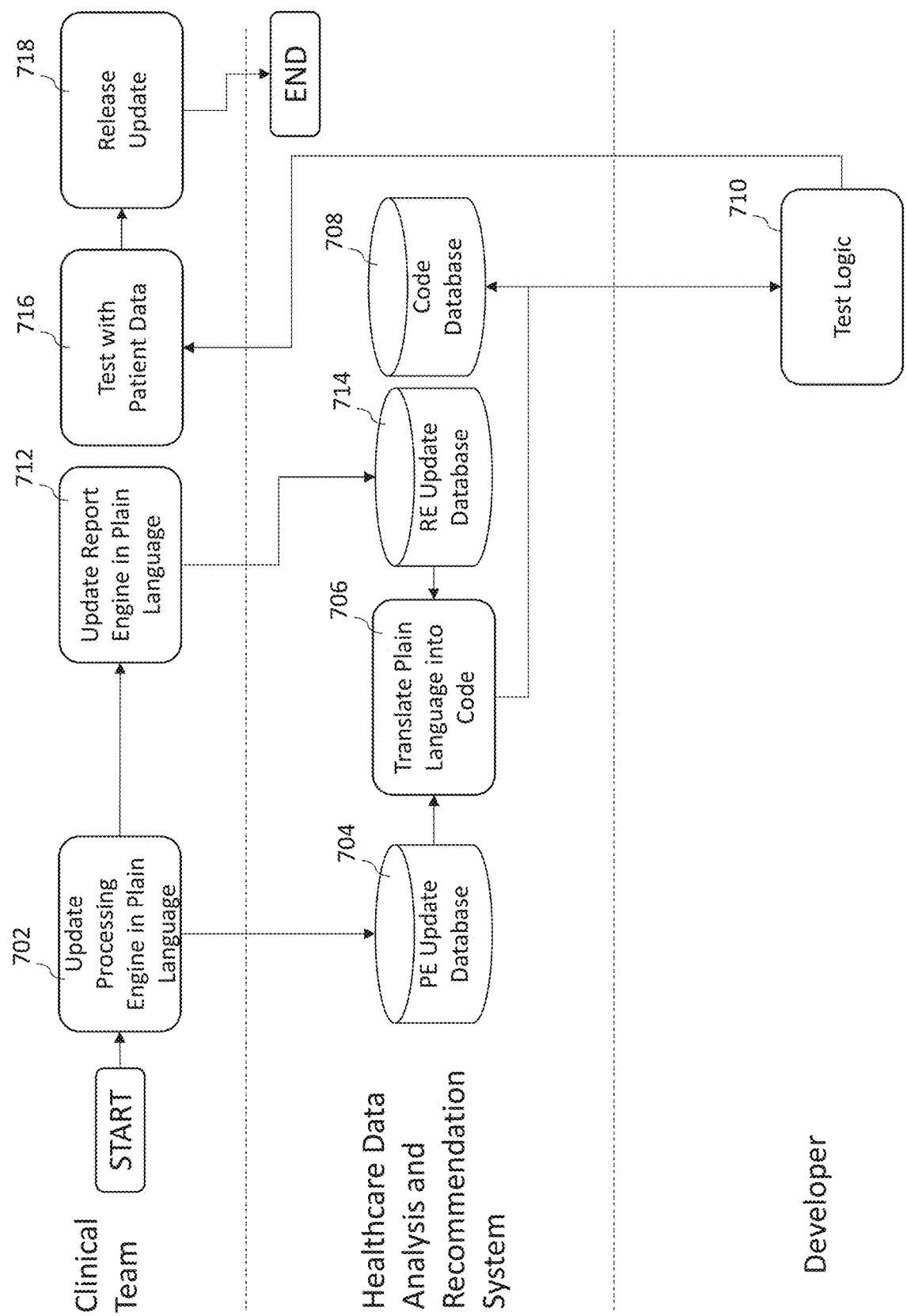

TREATMENT RECOMMENDATION LOGIC : VITAMIN D LAB TESTING

SYSTEMS, METHODS, AND DEVICES FOR AGGREGATED HEALTH DATA PROCESSING AND TREATMENT RECOMMENDATION GENERATION PLATFORMS

CROSS-REFERENCE TO RELATED APPLICATIONS

The present application claims the benefit under 35 U.S.C. 119(e) to U.S. Provisional Patent Application No. 62/576,230 filed Oct. 24, 2017, titled "SYSTEMS, METHODS, AND DEVICES FOR HEALTHCARE DATA ANALYSIS AND RECOMMENDATIONS," and U.S. Provisional Patent Application No. 62/576,268 filed Oct. 24, 2017, titled "SYSTEMS, METHODS, AND DEVICES FOR HEALTHCARE DATA ANALYSIS AND RECOMMENDATIONS," the entirety of which are hereby incorporated herein by reference under 37 CFR 1.57.

BACKGROUND

Field

The disclosure relates generally to the field of healthcare, and more specifically to systems, methods, and devices for healthcare data analysis and recommendations.

Description

Medical providers have been practicing prevention of heart attack, stroke and diabetes through identifying early risks for development of these diseases and through early identification of atherosclerosis through imaging and advanced blood laboratory markers. Identifying the overall risk, performing subsequent diagnostic imaging, laboratory, medication and lifestyle treatment options and educating patients is inherently complex due to a large amount of data intake and complex decision making based upon the data. Providing this level of care consistently is difficult due to time limitations in a fast-paced medical environment. Many patients will never be exposed to this level of care due to its complexity. To date, automated medical treatment systems have been unable to process and normalize varied and complex individual patient data to provide a high level of personalization and tailored patient reports and relevant educational materials. Thus, novel systems, methods, and devices for collecting and analyzing medical data through an automated and complex algorithmic system that quickly and efficiently provides treatment recommendations are needed.

SUMMARY

For purposes of this summary, certain aspects, advantages, and novel features of the invention are described herein. It is to be understood that not all such advantages necessarily may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

Some embodiments herein relate to a system for medical risk identification and generation of a dynamic patient health reporting interface, the system comprising: a processing engine configured to interface with a plurality of medical data sources, wherein at least one medical data source of the plurality of medical data sources comprises medical data having an incongruent data structure to another medical data source of the plurality of medical data sources, and wherein the medical data comprises one or more medical data types; a reporting engine configured to generate the dynamic patient health reporting interface and update the dynamic patient health reporting interface in response to a user input; one or more computer readable storage devices configured to store a plurality of computer executable instructions; and one or more hardware computer processors in communication with the one or more computer readable storage devices and configured to execute the plurality of computer executable instructions in order to cause the system to: collect and aggregate the medical data from one or more of the plurality of medical data sources; normalize, by the processing engine, the aggregated medical data into an operational data structure; perform, by the processing engine, an adaptive rule-based analysis of the normalized medical data to identify a patient medical risk level, wherein the rule-based analysis comprises both collectively and individually evaluating each medical data type of the normalized medical data; develop, by the processing engine, one or more patient treatment recommendations and/or treatment regimens based on the identified patient medical risk level; generate, by the reporting engine, the dynamic patient health reporting interface comprising a visual representation of the patient medical risk level and/or the one or more patient treatment recommendations and/or treatment regimens; display, to a user, the dynamic patient health reporting interface, wherein the dynamic patient health reporting interface comprises one or more interactive elements.

Some embodiments relate to a system, wherein the one or more interactive elements comprise at least an approval mechanism, wherein the approval mechanism can be activated by the user to select one or more patient treatment recommendations and/or treatment regimens.

Some embodiments herein relate to a system, wherein the reporting engine is further configured to programmatically generate and display, through the dynamic patient health reporting interface, a patient education plan upon activation of the approval mechanism.

Some embodiments herein relate to a system, wherein the one or more interactive elements comprise at least a modification mechanism, wherein the modification mechanism can be activated by the user to adjust the patient treatment recommendations and/or treatment regimens.

Some embodiments herein relate to a system, further comprising a data entry user interface configured to allow a user to input the medical data into the system.

Some embodiments herein relate to a system, wherein the data entry user interface is further configured to update through utilization of an application programming interface.

Some embodiments herein relate to a system wherein the data entry user interface is further configured to update through importation of medical data from a .CSV, .DOC, and/or .XLS file.

Some embodiments herein relate to a system, wherein importation can be completed for about 3000 users in a single instance.

Some embodiments herein relate to a system, wherein identifying the patient medical risk level comprises making at least one individual or aggregated lab, diagnostic, and/or biometric risk determination.

Some embodiments herein relate to a system, wherein identifying the patient medical risk level comprises calculating at least one risk calculation formula score.

Some embodiments herein relate to a system, wherein the one or more hardware computer processors is further configured to execute the plurality of computer executable instructions in order to cause the system to generate a unique activation code that allows a patient to access the dynamic patient health reporting interface.

Some embodiments herein relate to a system, wherein the one or more patient treatment recommendations and/or treatment regimens comprise at least one of sodium restrictions, specific food/drink recommendations, cardiovascular exercise, high intensity interval training (HIIT), strength training, flexibility training, weight lifting regimens, stress relief, sleep regimens, body composition improvement, quitting tobacco or assisting with other drug dependence, addiction rehabilitation, reduction of high cholesterol, high and/or low blood pressure treatment, recovery from heart attack and/or stroke, prevention of congestive heart failure, heart disease prevention, allergy treatment, prevention of cerebrovascular and/or cardiovascular disease, diabetes treatment, antithrombotic treatments, metabolism improvement, niacin deficiency treatment, treatment of sleep apnea and other sleep disorders, and/or uric acid disorders.

Some embodiments herein relate to a system, wherein the medical data comprises one or more of lipid profile data (e.g. Total Cholesterol (TC), Apolipoprotein E (APOE), low-density lipoprotein (LDL), high-density lipoprotein (HDL), triglycerides, lipoprotein a (Lp(a)), small dense LDL (sdLDL), cholesterol particle measurements), inflammation lab profile data (e.g. F2-Isoprostanes/Creatinine Ratio (F2-IsoPs), Oxidized low-density lipoprotein (oxLDL), ADMA, SDMA, Urinary Microalbumin/Creatinine Ratio (MACR), High-Sensitive C-Reactive Protein (hsCRP), Lipoprotein-associated phospholipase-A2 (LpPLA2), Lipoprotein-associated phospholipase-A2 Activity (LpPLA2 Activity), Myeloperoxidase (MPO)), microbiome labs (Trimethylamine N-oxide (TMAO)), insulin resistance and diabetes laboratory tests (e.g. Fasting Glucose, Total Insulin, Hemoglobin A1C (HbA1C), GlycoMark, Insulin Sensitivity, Homeostatic Model Assessment for Insulin Resistance (HOMA-IR), Beta Cell Function, Oral Glucose Tolerance Testing (OGTT)), myocardial laboratory tests markers (Galectin-3 (Gal-3), N-Terminal proBNP (proBNP), SMC Cardiac Troponin (hsTroponin), platelet function tests (11-dhTXB2/Creatinine), vitamin and supplement labs (Vitamin D, Vitamin B12, Folate, Homocysteine, Ubiquinol, Omega Check, other labs (Uric Acid, Creatine Kinase (CK), Thyroid Stimulating Hormine (TSH), genetics MTHFR, ApoE, Haptoglobin, KIF6, LPA Aspirin, CYP2C19, 4q25, 9p21), diagnostic data (e.g. Full or Limited Carotid, Carotid Intima-Media Thickness (CIMT), Endothelial Function test, Ankle-brachial Pressure Index (ABI), Calcium Artery Score (CACS), Abdominal Aortic Aneurysm Screening (AAA), Echocardiogram (ECHO), OralDNA/MyPeriopath, Obstructive Sleep Apnea test), biometric data (weight, height, BMI, neck circumference, waist circumference, blood pressure, pulse), patient history (e.g. ethnicity, blood type, history of infections, past medical events, medical diagnoses, sexual health functions, smoking history, alcohol consumption history), lifestyle habits (nutrition, exercise, sleep habits, stress level assessment, socioeconomic assessment, weight history, oral health habits), and/or the various input variables listed in Appendix A.

Some embodiments herein relate to a system, wherein the patient medical risk level comprises clinical risk identification for at least one of heart attack, stroke and diabetes.

Some embodiments herein relate to a system, wherein the dynamic patient health reporting interface further comprises one or more medication, treatment, preventative, health, lifestyle, and behavioral recommendations.

Some embodiments herein relate to a system, further comprising a report approval interface configured to allow a user to approve, modify, and/or reject the generated dynamic patient health reporting interface comprising.

Some embodiments herein relate to a system, wherein the processing engine and/or the reporting engine are configured to be updated with plain-language logic.

Some embodiments herein relate to a system, wherein and system is configured to automatically translate the plain language into executable code.

Some embodiments herein relate to a system, wherein at least one of the plurality of medical data sources comprises an electronic health record (EHR).

Some embodiments herein relate to a system, wherein the medical data types comprise at least the following: diagnostic data, historic population data, historic patient data, lab testing data, medication data, lifestyle data, biographical data, and medical imaging data.

Some embodiments herein relate a system, wherein identifying the patient medical risk level comprises: determining whether CIMT plaque type test results are available to the system; and determining the patient medical risk level based on the type of plaque indicated in the CIMT plaque type test results; wherein no plaque identifies a low risk; wherein hard, calcified, or echogenic plaque identifies a moderate risk; wherein mixed or heterogeneous plaque identifies a high risk; and wherein homogeneous or soft plaque identifies a very high risk.

Some embodiments herein relate a system, wherein identifying the patient medical risk level comprises: calculating a patient CIMT percentile, wherein calculating the patient CIMT percentile comprises: solving a linear equation to estimate CIMT for patients aged 40-70 at a 5th, 10th, 25th, 50th, 75th, 90th, and 95th percentile; and creating and solving a piecewise function to compute the patient CIMT percentile.

Some embodiments herein relate a system, wherein identifying the patient medical risk level comprises: calculating a patient CIMT age, wherein calculating the patient CIMT age comprises: obtaining one or more parameters by solving a linear equation using the 50th percentile CIMT across patients aged 40-70; and calculating the patient CIMT using the one or more parameters.

BRIEF DESCRIPTION OF THE DRAWINGS

The foregoing and other features, aspects, and advantages of the present invention are described in detail below with reference to the drawings of various embodiments, including the appendices submitted herewith, which are intended to illustrate and not to limit the invention. The drawings comprise the following figures in which:

FIG. 1B illustrates another example data entry user interface according to various embodiments described herein;

FIG. 1C illustrates another example data entry user interface according to various embodiments described herein;

FIG. 2 illustrates an example report approval portal according to various embodiments described herein;

FIG. 3A illustrates an example report approval interface according to various embodiments described herein;

FIG. 3B illustrates another example report approval interface according to various embodiments described herein;

FIG. 3C illustrates another example report approval interface according to various embodiments described herein;

FIG. 5B illustrates a portion of another example patient report interface according to various embodiments described herein;

FIG. 7 illustrates a flow chart of an example system logic update process according to various embodiments herein;

DETAILED DESCRIPTION OF THE EMBODIMENTS

Figure 1A:
FIG. 1A illustrates an example data entry user interface according to various embodiments described herein.

Although several embodiments, examples, and illustrations are disclosed below, it will be understood by those of ordinary skill in the art that the invention described herein extends beyond the specifically disclosed embodiments, examples, and illustrations and includes other uses of the invention and obvious modifications and equivalents thereof. Embodiments of the invention are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described.

Identifying health risks, conducting subsequent imaging and laboratory tests, providing medication and lifestyle treatment options and educating patients is an inherently complex and long-term process due to a large amount of data intake and complex decision making required. Providing this level of care consistently is difficult due to time limitations in a fast-paced medical environment. Many patients may never be exposed to this level of care due to its complexity. To date, automated medical treatment systems have been unable to process and normalize varied and complex individual patient data to provide a high level of personalization and tailored patient reports and relevant educational materials. Thus, novel systems, methods, and devices for collecting and analyzing medical data through an automated and complex algorithmic system that quickly and efficiently provides treatment recommendations are needed.

Some embodiments described herein are directed to a universal health platform that may efficiently provide sophisticated health data processing and treatment recommendations. In some embodiments, the platform may be configured to allow a user (e.g. a patient or health professional) to input or import a vast and varied collection of data including health, medical, lifestyle, historical, and other relevant data. In some embodiments, the platform may be configured to process this data through a multifaceted and dynamically updated decision-making protocol to create a personalized patient report. In some embodiments, the personalized patient report may comprise various medications, treatment, preventative, health, lifestyle, behavioral, other recommendations and/or plans. In some embodiments, the data input and personalized patient report features are communicated to a user through a dynamic user interface configured to automatically update and adjust based on newly inputted data and/or user selection and/or rejection of recommendations in the personalized patient report. In some embodiments, the dynamic user interface may also be configured to link to various information sources including, for example, education portals that provide patients with further information regarding treatment regimens or medications.

Some embodiments disclosed herein provide a process and/or cloud-based software application and/or system for use in the biotechnology, medical and/or wellness industries. In some embodiments, the system is configured to execute specific methods and/or rules, as disclosed herein, for processing patient health data in order to generate a dynamic report interface comprising one or more specific recommendations and/or treatment regimens and/or plans for a patient. In some embodiments, the systems, methods, and devices described herein accumulate patient health data from various sources, evaluate the data collectively and independently, and implement complex decision making protocols to generate patient health reports and treatment/health recommendations.

In some embodiments, a system as disclosed herein is configured to collect (or otherwise access) diagnostic and/or laboratory data, analyze the diagnostic and/or laboratory data, and make suggestions for treatments to patients and/or medical providers based upon diagnostic and laboratory results. In some embodiments, the data analyzed comprises a relatively large number of data points and entails complex decision making implemented at least partially in one or more novel algorithms disclosed herein. One advantage of the systems as disclosed herein is that, in some embodiments, the systems can be configured to analyze data faster and/or more completely by, among other things, applying the specific methods and/or rules set forth herein.

In some embodiments, the system implements clinical risk identification for heart attack, stroke and diabetes. In some embodiments, the system acts as a clinical decision-making tool for medical providers, and/or a personalized education tool based upon a personalized plan for the patient (and/or the results of the system's analysis and a medical provider plan).

In some embodiments, the system is configured to collect data from patient medical and/or social history, family history, patient questionnaire, laboratory markers, diagnostic imaging, and/or the like. Based upon this information, the system can be configured to use one or more algorithms to analyze the data and determine the patient risk level and/or additional diagnostic tests and advanced laboratory markers that the medical provider should consider ordering for the patient.

In some embodiments, the system can be configured to collect and analyze, both collectively and independently, lab testing data, patient health data, patient social history, lifestyle habits, patient questionnaire data, laboratory markers, diagnostic imaging data, family history data, medication history, nutrition supplement intake, biometric data and/or the like. For example, the system may be configured to collect and analyze: lipid profile data (e.g. Total Cholesterol (TC), Apolipoprotein E (APOE), low-density lipoprotein (LDL), high-density lipoprotein (HDL), triglycerides, lipoprotein a (Lp(a)), small dense LDL (sdLDL), cholesterol particle measurements), inflammation lab profile data (e.g. F2-Isoprostanes/Creatinine Ratio (F2-IsoPs), Oxidized low-density lipoprotein (oxLDL), ADMA, SDMA, Urinary Microalbumin/Creatinine Ratio (MACR), High-Sensitive C-Reactive Protein (hsCRP), Lipoprotein-associated phospholipase-A2 (LpPLA2), Lipoprotein-associated phospholipase-A2 Activity (LpPLA2 Activity), Myeloperoxidase (MPO)), microbiome labs (Trimethylamine N-oxide (TMAO)), insulin resistance and diabetes laboratory tests (e.g. Fasting Glucose, Total Insulin, Hemoglobin A1C (HbA1C), GlycoMark, Insulin Sensitivity, Homeostatic Model Assessment for Insulin Resistance (HOMA-IR), Beta Cell Function, Oral Glucose Tolerance Testing (OGTT)), myocardial laboratory tests markers (Galectin-3 (Gal-3), N-Terminal proBNP (proBNP), SMC Cardiac Troponin (hsTroponin), platelet function tests (11-dhTXB2/Creatinine), vitamin and supplement labs (Vitamin D, Vitamin B12, Folate, Homocysteine, Ubiquinol, Omega Check, other labs (Uric Acid, Creatine Kinase (CK), Thyroid Stimulating Hormine (TSH), genetics MTHFR, ApoE, Haptoglobin, KIF6, LPA Aspirin, CYP2C19, 4q25, 9p21), diagnostic data (e.g. Full or Limited Carotid, Carotid Intima-Media Thickness (CIMT), Endothelial Function test, Ankle-brachial Pressure Index (ABI), Calcium Artery Score (CACS), Abdominal Aortic Aneurysm Screening (AAA), Echocardiogram (ECHO), OralDNA/MyPeriopath, Obstructive Sleep Apnea test), biometric data (weight, height, BMI, neck circumference, waist circumference, blood pressure, pulse), patient history (e.g. ethnicity, blood type, history of infections, past medical events, medical diagnoses, sexual health functions, smoking history, alcohol consumption history), lifestyle habits (nutrition, exercise, sleep habits, stress level assessment, socioeconomic assessment, weight history, oral health habits), the various input variables listed in Appendix A, and/or any other relevant data points.

In some embodiments, completed diagnostic imaging and laboratory test data can be inserted, imputed, and/or imported into the system. Some or all patient data collected can be used to assess the patient's risk level with new information. In some embodiments, one or more sophisticated algorithms can be used to recommend medication, supplement and/or lifestyle treatments that the medical provider may consider or implement for the patient to decrease a risk of heart attack, stroke or diabetes in the present and/or the future of the patient.

In some embodiments, the system may generate preventive and therapeutic medical recommendations, treatment plans, and general medical, lifestyle, and/or health recommendations. For example, the system may dynamically generate a meal plan based on, for example, patient nutritional measurements, dietary restrictions, allergies, biometric measurements, medical history, laboratory data, exercise habits, genetic markers, and/or the like. In some embodiments, the system may generate plans and/or recommendations including, for example, sodium restrictions, specific food/drink recommendations (e.g. dark chocolate, cinnamon, water, or vegetable intake recommendations), cardiovascular exercise, high intensity interval training (HIIT), strength training, flexibility training, and/or weight lifting regimens, stress management, sleep regimens, body composition improvement, quitting tobacco or assisting with other drug dependence, addiction rehabilitation, reduction of high cholesterol (e.g. statin prescription, nicotinic acid supplementation, plant sterol supplementation), high and/or low blood pressure treatment (e.g. Ramipril prescription), recovery from heart attack and/or stroke, prevention of congestive heart failure, heart disease prevention, allergy treatment, prevention of cerebrovascular and/or cardiovascular disease, diabetes and insulin resistance treatment (e.g. Metformin and/or Pioglitazone prescriptions, blood sugar regulation, fiber supplementation, vitamin and/or mineral supplementation (e.g. Vitamin A, B, C, D, E, K, folic acid, and/or calcium recommendations)), antithrombotic treatments (e.g. antiplatelet and/or anticoagulant prescriptions), metabolism improvement (e.g. Coenzyme Q10 supplementation), treatment of sleep apnea and other sleep disorders, uric acid disorders (e.g. gout, hypouricemia, and/or hyperuricemia), lifestyle recommendations (including, for example, recommendations, treatment options, and explanations found in Appendix A), medication supplement recommendations (including, for example, medications, treatment options, and explanations found in Appendix A), diagnostic, lab, and follow-up testing recommendations (including, for example, the tests, treatment options, and explanations in Appendix A), health coaching, test plans, and those shown in Appendix A, among others.

In some embodiments, the system can enable a user (e.g. medical provider, allied health professional, etc.) to review recommended treatments and approve the treatments he/she assesses are in the best interest of the patient. In some embodiments, a medical provider or allied health professional's plan may be approved and an education plan on the patient's test results and the medical provider or allied health professional's approved plan can be made available to the patient on, for example, a cloud-based website for patient view and further education.

In some embodiments, if an individual is unable to obtain access to the system herein from their own provider, the system can be configured to comprise an automated feature that will collect data from the individual, make recommendations for advanced laboratory and diagnostic testing, provide the results, a lifestyle plan and medical recommendations to discuss with their own medical provider. In some embodiments, the platform can be implemented to assess data and provide reports to groups, such as corporate groups, or direct-to-consumer.

In some embodiments, large amounts of data are captured and stored by the systems disclosed herein. This data can, for example, be used to create new medical logic and/or algorithms as the data increases to statistical significance. In some embodiments, the systems disclosed herein may comprise one or more data entry interfaces configured to allow patient data entry by users. In some embodiments, the systems described herein can be configured to allow importation of data from one or more external databases, including, for example, electronic health records (EHR) and/or blockchain databases. As used herein, blockchain database may refer to any distributed ledger database that is spread across several nodes or computing devices, wherein each node may copy and store an identical duplicate of the ledger, and wherein each node of a network may update itself independently. Blockchain databases, as used herein are not limited to distributed ledgers that employ a chain of blocks. As used herein, "blockchain database" may be synonymous with "distributed ledger database." In some embodiments, a blockchain database may be distributed across and managed by one or more peer-to-peer networks and may exist without a centralized authority or central server. In some embodiments, patient data can be acquired through utilization of an application programming interface (API) (e.g. ICD-10 code API, medication API, etc.). In some embodiments, utilization of one or more APIs may allow the systems described herein to interface with standardized medical databases and other sources of patient data. In some embodiments, one or more APIs are used to exchange data between an EHR database, blockchain database, external databases, and/or vendor databases to transfer data from one database to another. In some embodiments, a user action, such as generating a plan approval, approving a treatment plan, opening a patient chart, searching scheduled appointment lists, within the systems described herein, EHR, and/or blockchain platform, may cause the systems to transfer data between one or more of the databases described herein. In some embodiments, the transferred data could include data such as medications, medication allergies, diagnosis codes, family history, social history, demographics, biometric measurements, any of the input variable of Appendix A, and the like.

In some embodiments, the systems, methods, and devices described herein can be configured to utilize input variables and formulas to create medical decision-making logic for heart attack, stroke and diabetes prevention.

In some embodiments, the systems, methods, and devices described herein provide treatment information to a medical provider through a cloud-based web application. In some embodiments, the systems described herein can be configured to allow a medical provider to complete a system-generated plan approval, which can lead to implementation of the system-generated plan.

In some embodiments, the patient portal can be populated with education and test results for patient viewing.

In some embodiments, the system can be utilized for individuals, small or large groups, such as corporate groups, or entire populations with automated algorithmic logic that may create a lifestyle plan and medical recommendations.

In some embodiments, the system can be used as a facilitation tool between an individual or group and a medical provider.

In some embodiments, the system can determine specific advanced laboratory and diagnostic testing to be offered through the system without a medical provider directly involved.

Data Entry Interface and Importation

In some embodiments, the platform comprises a data entry user interface (UI) or patient chart configured to allow a user (e.g. patient, employee, or medical professional) to input medical data into the system. FIG. 1A illustrates an example data entry user interface 100A according to various embodiments described herein. In some embodiments, the platform comprises various data entry tabs 102, including, for example, reports, basic info, alerting labs, basic labs, biometrics, advanced labs, tests, appointments, history, medications, lifestyle, orders, CIMT, HRA, and docs, among others. In some embodiments, selecting one of the data entry tabs 102 may cause the platform to display various data entry fields 104 corresponding to the specific selected data entry tab. In some embodiments, a user may enter relevant response information into the data entry fields 104.

Figure 1B:
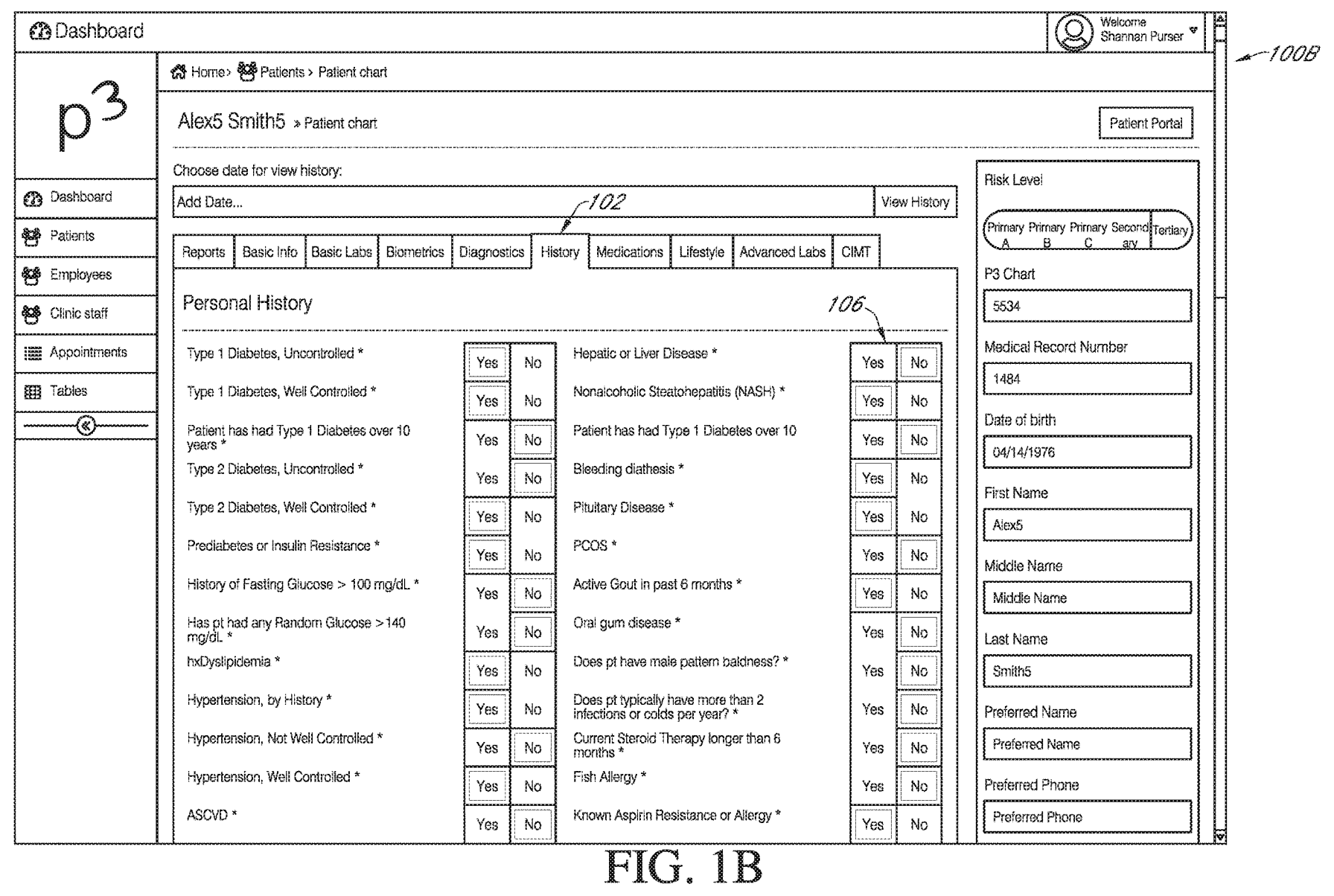

FIG. 1B illustrates another example data entry user interface 100B according to various embodiments described herein. In some embodiments, selecting one of the data entry tabs 102 may cause the platform to display one or more binary selections 106 (e.g. yes/no) or one or more other data entry mechanisms, which may be selected to enter patient data.

Figure 1C:
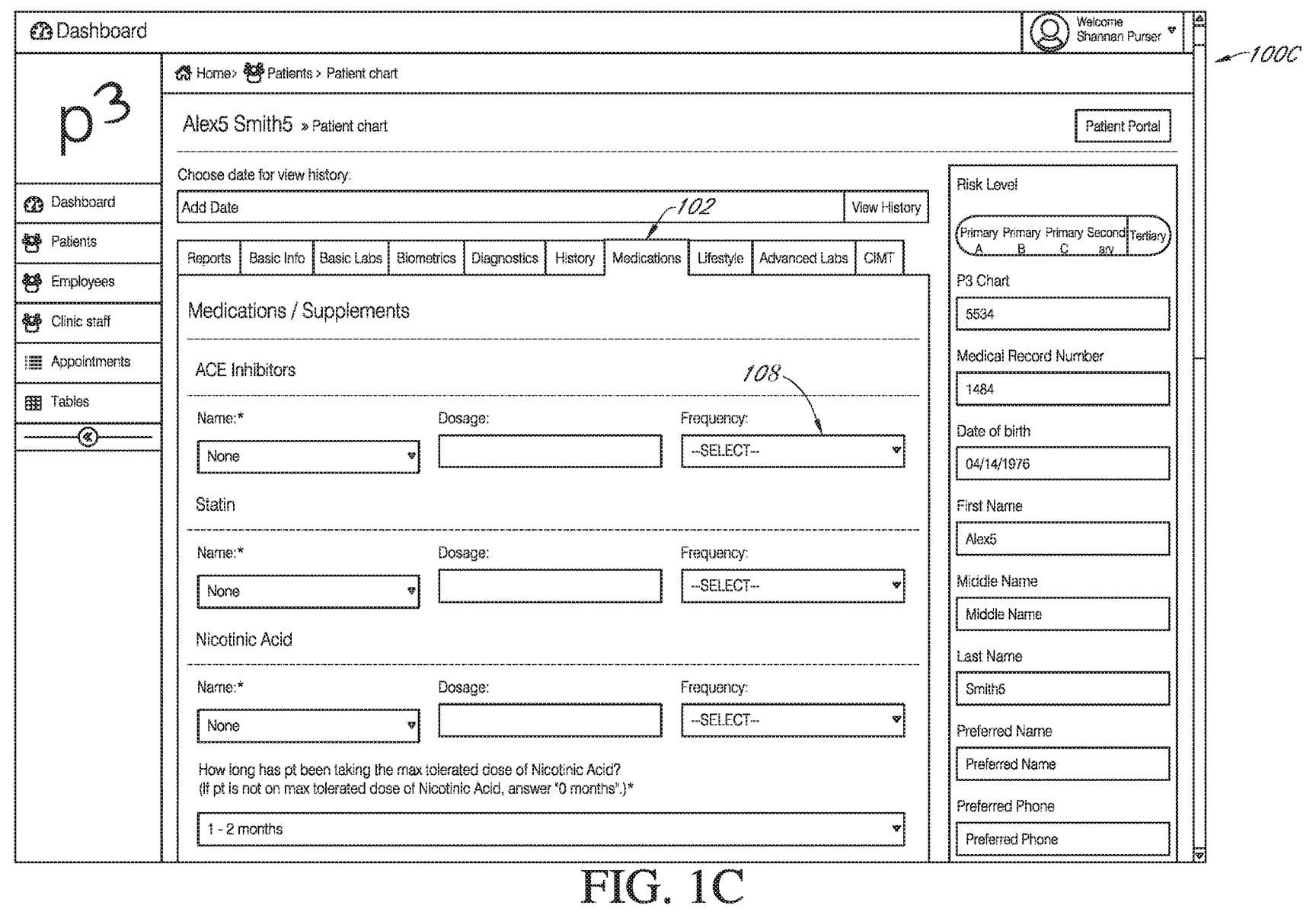

FIG. 1C illustrates another example data entry user interface 100C according to various embodiments described herein. In some embodiments, selecting one of the data entry tabs 102 may cause the platform to display one or more drop-down menus 108, which may allow entry of patient data through selection of one or more choices from a plurality of choices in the drop-down menu 108.

In some embodiments, data entry may comprise one or more of entering responses into data entry fields 104, making binary selections 106, selecting choices from a drop-down menu 108, and/or any other suitable data entry method. In some embodiments, the data entry interface or patient chart may be customized (e.g. adding, removing, modifying queries, data entry fields, binary selections, drop-down menus, etc.) through a user interface of the platform.

In some embodiments, the data entry user interface or patient chart may be updated through utilization of an application programming interface (API) (e.g. ICD-10 code API, medication API, etc.). In some embodiments, utilization of an API may increase efficiency by providing the platform with the capability to interface with standardized medical databases and other sources of patient data.

In some embodiments, additional patient data can be collected through, for example, patient surveys. In some embodiments, the patient survey can be deployed through the platform. In some embodiments, the platform can be configured to allow a patient to login via email or through a unique activation code sent to the patient to complete a patient survey. In some embodiments, an email or other electronic communication can be sent automatically upon a patient account creation, the email or other electronic communication containing, for example, a link to create a password or a unique activation code generated by the platform and provided to a patient to log in with, for example, the activation code, name, DOB and/or last 4 digits of SSN. In some embodiments, the platform may be configured to allow a patient to complete a patient survey through the data entry interface or patient chart within the platform. In some embodiments, a unique activation code can be generated by the platform that allows a patient to access the platform without utilization of an email address. In some embodiments, the patient survey function of the platform may enable a patient to complete about 90% of the data entry in the data entry interface. In some embodiments, the patient survey function of the platform may enable a patient to complete between about 0% and 90% of the data entry in the data entry interface. In some embodiments, the patient survey function of the platform may enable a patient to complete about 0%, 10%, 20%, 30%, 40%, 50%, 60%, 70%, 80%, or 90% of the data entry in the data entry interface, including any value between the aforementioned values. In some embodiments, the patient survey function of the platform may reduce costs for the patient, reduce workload of healthcare providers, and provide increased accuracy of the entered patient data. In some embodiments, the patient survey may be customized (e.g. by removing, adding, modifying questions) through a user interface of the platform to meet the specific needs of health providers and patients.

In some embodiments, data can be imported into the system from a supported file format, such as, e.g. .CSV, .DOC, .XLS, among others. In some embodiments, the results of the import can be displayed on the user interface and a more detailed preview can be found in a resulting spreadsheet. In some embodiments, importation of data can be completed for about or at least 3000 users in a single instance. In some embodiments, importation of data can be completed for about or at least 1, 2, 3, 4, 5, 6, 7, 8, 9, 10, 20, 30, 40, 50, 60, 70, 80, 90, 100, 200, 300, 400, 500, 1000, 2000, or 3000 users in a single instance, or any value between the aforementioned values.

In some embodiments, data can be imported from one or more external databases, including, for example, health provider databases, Electronic Health Record (EHR) databases, laboratory databases, research databases, census databases, blockchain databases, and the like.

In some embodiments, the system can be configured to validate imported data and dynamically generate and display a computer notification to a user, the computer notification containing a communication regarding the success or failure of the importation. In some embodiments, data importation may fail validation as a result of, for example, incorrect data format, missing mandatory fields, and failure of variable validation, among others.

In some embodiments, successful data importation may result in triggering of an automatic report generation or update. In some embodiments, a patient's health report and recommendations can be automatically updated or newly generated upon successful data input or importation from a supported file format and/or another external source. In some embodiments, patient data may be acquired through one or more of data entry, importation, and/or any other data acquisition method.

Some embodiments herein relate to the collection of user information from various disparate databases, data entries, and data importations. In some embodiments, the systems, methods, and devices herein are directed to interfacing with a plurality of disparate databases and/or information sources which store data having a plurality of incongruent data structures. In some embodiments, the systems and devices herein may be configured to interface with these data structures and conduct a normalization process to transform the data into one or usable, integrated data structures. In some embodiments, normalization of the patient data can increase the accuracy and efficiency of processing and analyzing the data and generating a personalized patient report. In some embodiments, normalizing the patient data retrieved from the one or more databases, data entries, or imported data comprises translating a data structure of the retrieved patient data from the one or more databases, data entries, or imported data. In some embodiments, data may be obtained through an API, blockchain database, and/or HL7 interfaces. In some embodiments, the data may be received through JavaScript, HL7, Python, Java, HTML, readable PDF, CSV file, and the like. In some embodiments, the received data may be sent through a translator function. In some embodiments, the translator parses data according to one or more defined translation protocols to identify the type of data points available for translation. In some embodiments, the translator transforms the identified data points into code that the system, including a processing engine and/or reporting engine, can read (e.g. JSON, JavaScript, HTML, etc.). In some embodiments, the translated data can be transmitted to the system for further processing and use in the algorithms and/or functions described herein.

Report Generation and Approval Interface

In some embodiments, the platform comprises a processing engine and report/reporting engine configured to process and analyze the inputted or imported data and dynamically generate a personalized patient report to be displayed through a dynamic user interface.

In some embodiments, the platform can be configured to utilize raw or normalized patient data in one or more sophisticated diagnosis and treatment algorithms. In some embodiments, the platform, through processing of the patient data using the algorithms, can be configured to make one or more determinations regarding risk factors, need for testing, recommended treatments, and/or overall health of a patient, among others. Based on the one or more determinations, the platform can generate a personalized patient report comprising one or more preventative, diagnostic, medication, lifestyle, behavior, or treatment recommendations. In some embodiments, the personalized patient report can comprise multiple reports (e.g. lifestyle plan, medication recommendations, testing recommendations, etc.) for increased focus on specific health aspects and patient understanding of the recommendations therein.

Figure 2:
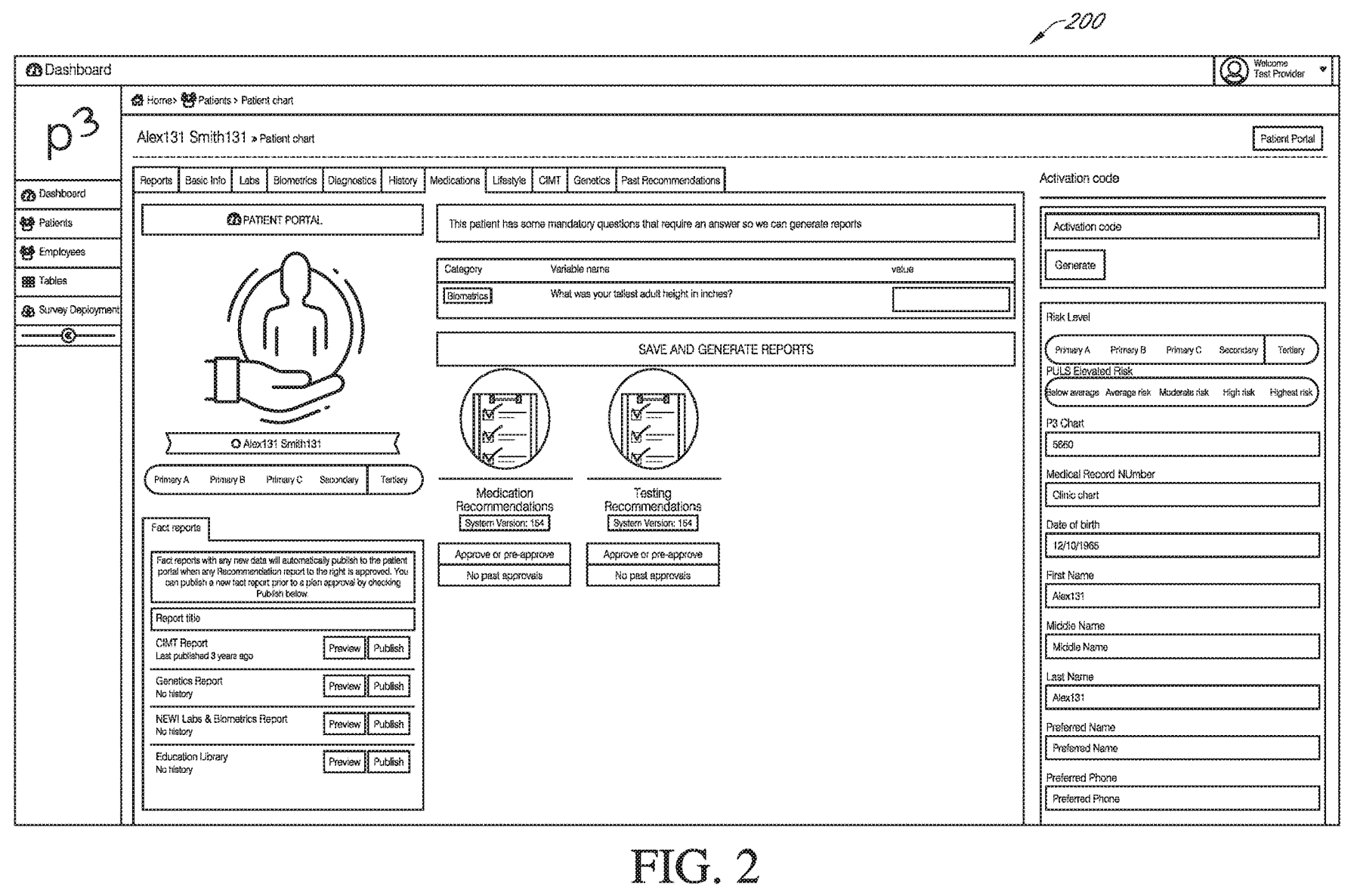

FIG. 2 illustrates an example report approval portal 200 according to various embodiments described herein. In some embodiments, generated reports can be subjected to an approval mechanism, wherein a health provider may review the reports prior to the reports being displayed to the patient. In some embodiments, generated reports may be pre-approved such that manual approval is not required and the report can be displayed automatically upon creation to a patient.

Figure 3A:
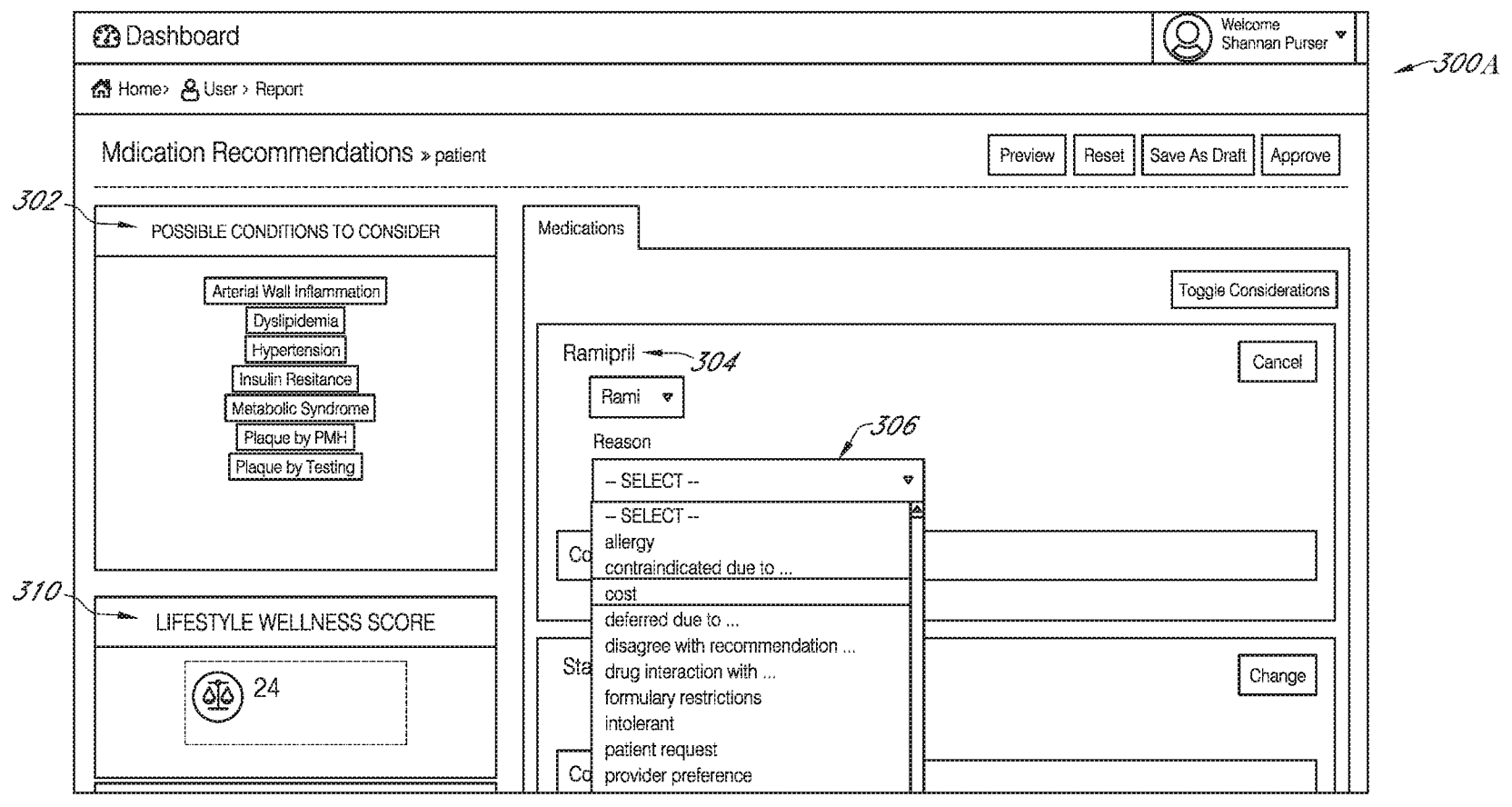

In some embodiments, the reports can be manually or automatically altered or updated according to user selections. FIG. 3A illustrates an example report approval interface 300A for medication recommendations according to various embodiments described herein. In some embodiments, the report approval interface can be configured to allow a user to view the various health considerations 302 (e.g. determinations resulting from sophisticated algorithms such as those in, for example, FIGS. 8A-8C, 9-15, and Appendix A) used by the platform to form recommendations. In some embodiments, the report approval interface is configured to display to a user the platform-generated recommendation 304 regarding a health aspect (e.g. medication, exercise, diet, etc.) and may comprise a modification mechanism 306 for altering or updating the recommendation. For example, the recommendations may be altered because a health professional may disagree with a given platform recommendation, because the cost of a recommended medication is prohibitive, because of a patient request, or because of various other reasons for which the platform may have insufficient data to fully consider. In some embodiments, the report approval interface may comprise various biometrics 308 (see, e.g. FIG. 3B) and a lifestyle wellness score 310 (e.g. calculated according to the algorithms and/or calculations in the chart titled "p3 Score Functions" in Appendix A), which may comprise a numerical value representing a patient's overall health. In some embodiments, the report approval interface may be configured to allow a user to indicate final approval of a report. In some embodiments, an approved report can be displayed to a patient through a dynamic user interface of the platform.

Figure 3B:
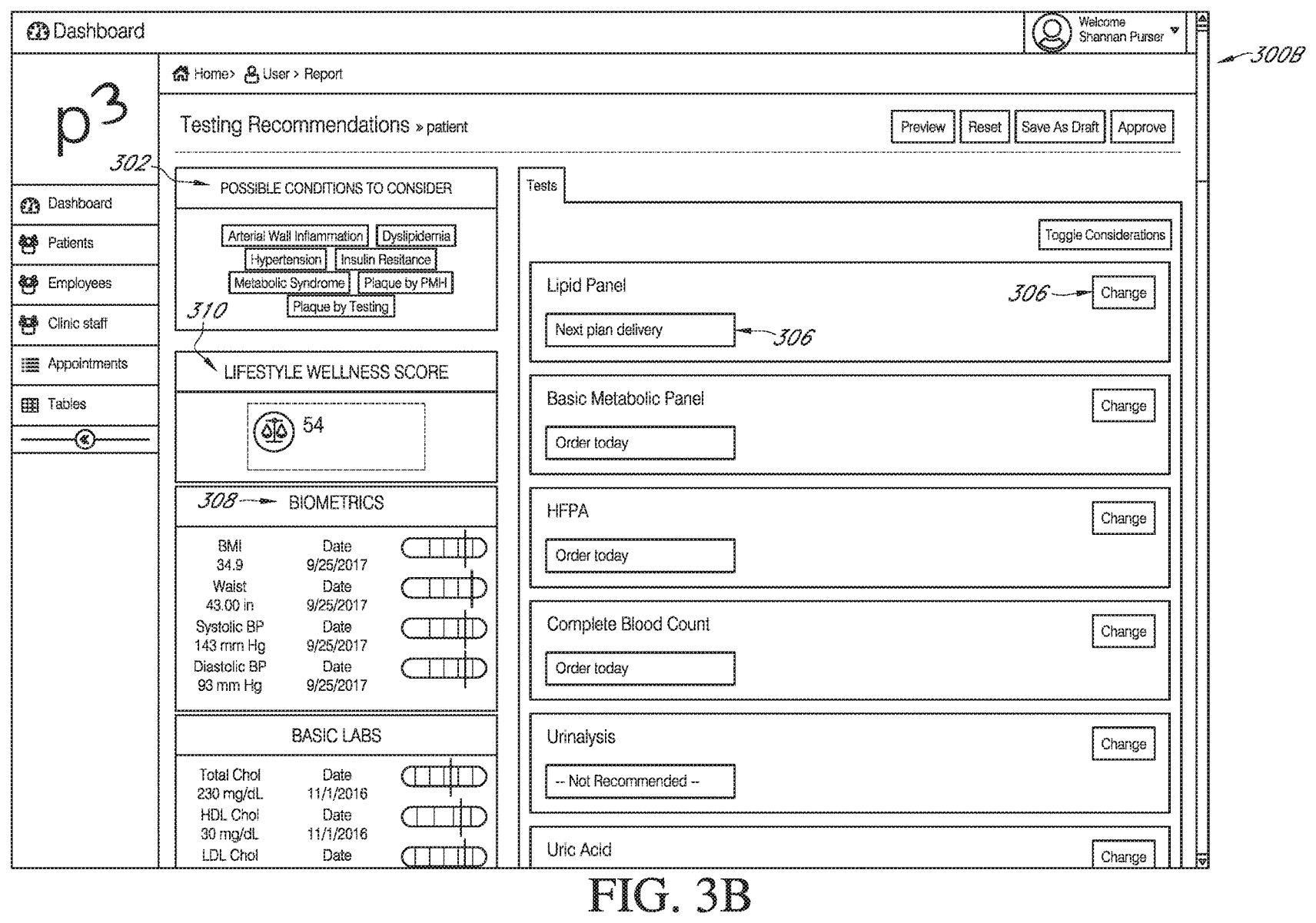

FIG. 3B illustrates another example report approval interface for platform generated testing recommendations according to various embodiments described herein. In some embodiments, the report approval interface may comprise one or more modification mechanisms 306 configured to allow a user to select approve or modify recommended actions based on the health determinations made by the platform.

Figure 3C:
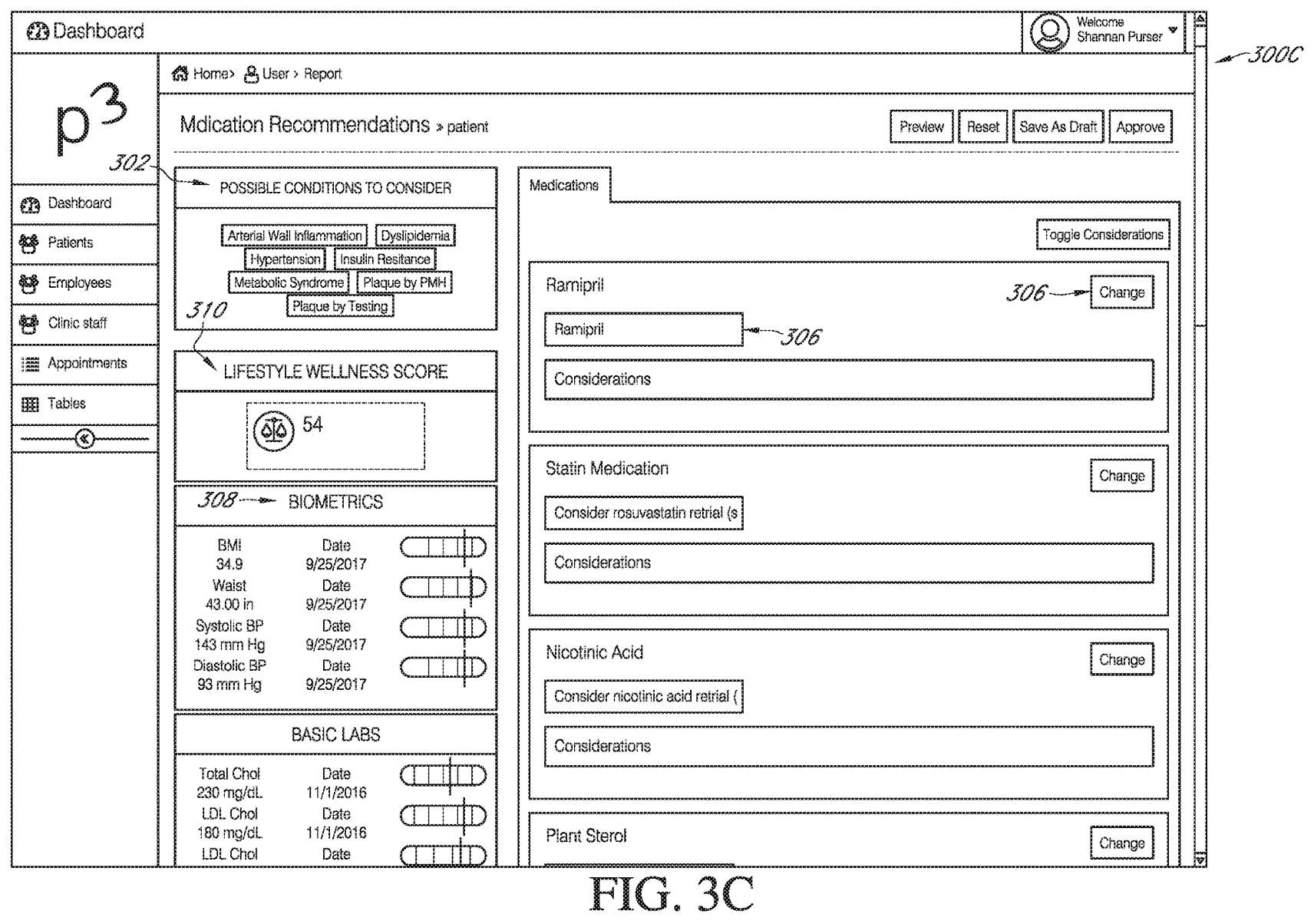
Figure 3D:
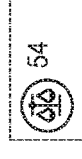
FIG. 3D illustrates another example report approval interface according to various embodiments described herein.

FIG. 3C illustrates another example report approval interface for medication recommendations according to various embodiments described herein. FIG. 3D illustrates another example report approval interface for a lifestyle plan according to various embodiments described herein.

In some embodiments, certain reports may not require approval and can be published automatically by the platform upon generation. For example, static reports (e.g. reports containing only static widgets as described below) without treatment recommendations may publish automatically to the patient rather than manually upon approval by a health provider. In some embodiments, a threshold level of approval needed to publish reports can be defined by a user.

Patient Report Interfaces

Figure 4:
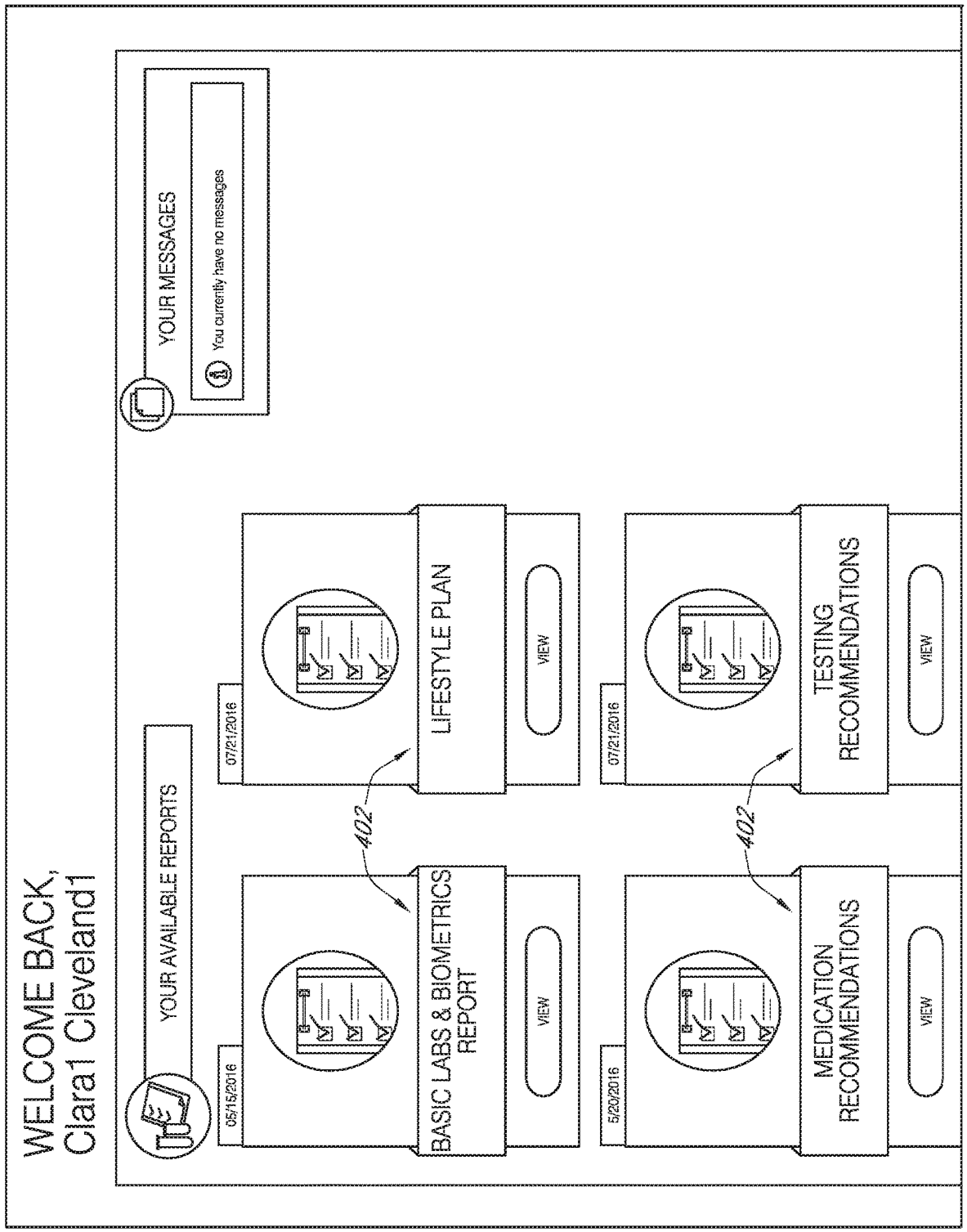
FIG. 4 illustrates an example patient report portal according to various embodiments described herein.

FIG. 4 illustrates an example patient report portal 400 according to various embodiments described herein. In some embodiments, the patient report portal can be configured to be populated by generated and/or approved patient reports 402. In some embodiments, the patient report portal serves as a central hub for patients to select and access the available patient reports.

Figure 5A:
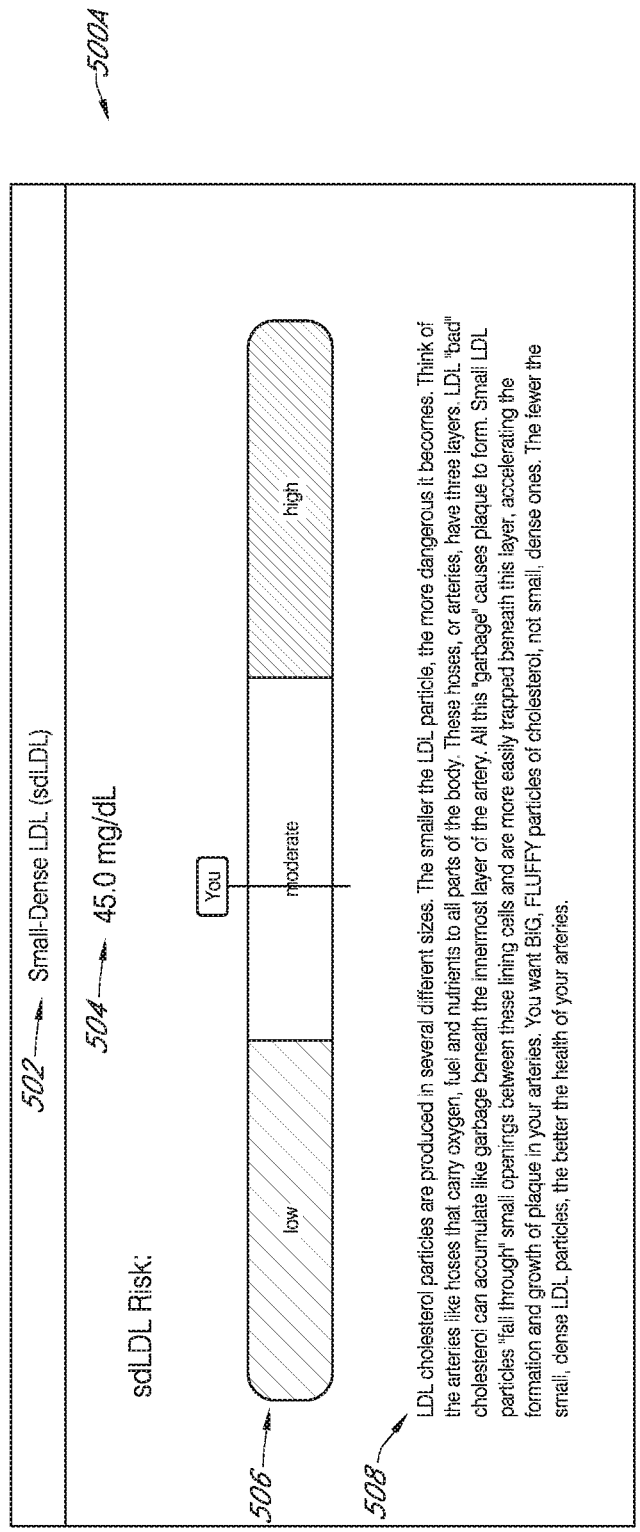
FIG. 5A illustrates a portion of an example patient report interface according to various embodiments described herein.

FIG. 5A illustrates a portion of an example patient report interface 500A according to various embodiments described herein. The patient report interface may comprise widgets including information regarding health conditions, patient condition, treatments, recommendations, plans, educational materials, interactive elements, approval or modification mechanisms, and other elements. For example, example patient report interface 500A comprises a condition/treatment/recommendation/plan title 502 which summarizes the contents of the portion of the example patient report interface, a patient value or action 504 which comprises a patient's tested or determined value or condition (e.g. sdLDL) or a recommended action, a risk indicator 506 which summarizes a degree of risk to the patient based on the patient value or action 504 and other determinations made by the platform, and an education summary 508 which provides education material regarding the condition, test, risks, treatment, recommendation, plan or other relevant subject matter. In some embodiments, one or more of the elements described above, including, for example, the condition/treatment/recommendation/plan titles 502, risk indicator 506, patient value or action 504, and/or education summary 508 may comprise one or more interactive elements, such as a hyperlink or other functional mechanism that, when selected by a user, opens a web page, dialog box, chat window, product page, drug information sheet, or other education materials or report functions.

FIG. 5B illustrates another portion of an example patient report interface 500B according to various embodiments described herein. In addition to the widget elements described above, the patient report interface may comprise one or more section headings 510 which summarize the contents or purpose one or more sections of the report, section subheadings 512 which further summarize the contents or purpose one or more subsections of the report, and one or more alerts 514 which alert a patient to potential risks or considerations regarding the recommendations, plans, and the like contained in the report. In some embodiments, the above elements, including one or more section headings 510, section subheadings 512, and one or more alerts 514 may also comprise interactive elements. In some embodiments, the patient report interface may comprise additional and/or different elements and interactive elements than those shown.

In some embodiments, the patient report interface can be customized according to the individual capabilities and needs of a user (e.g. patient, corporate group, health provider, etc.).

End User Data Collection

Figure 6A:
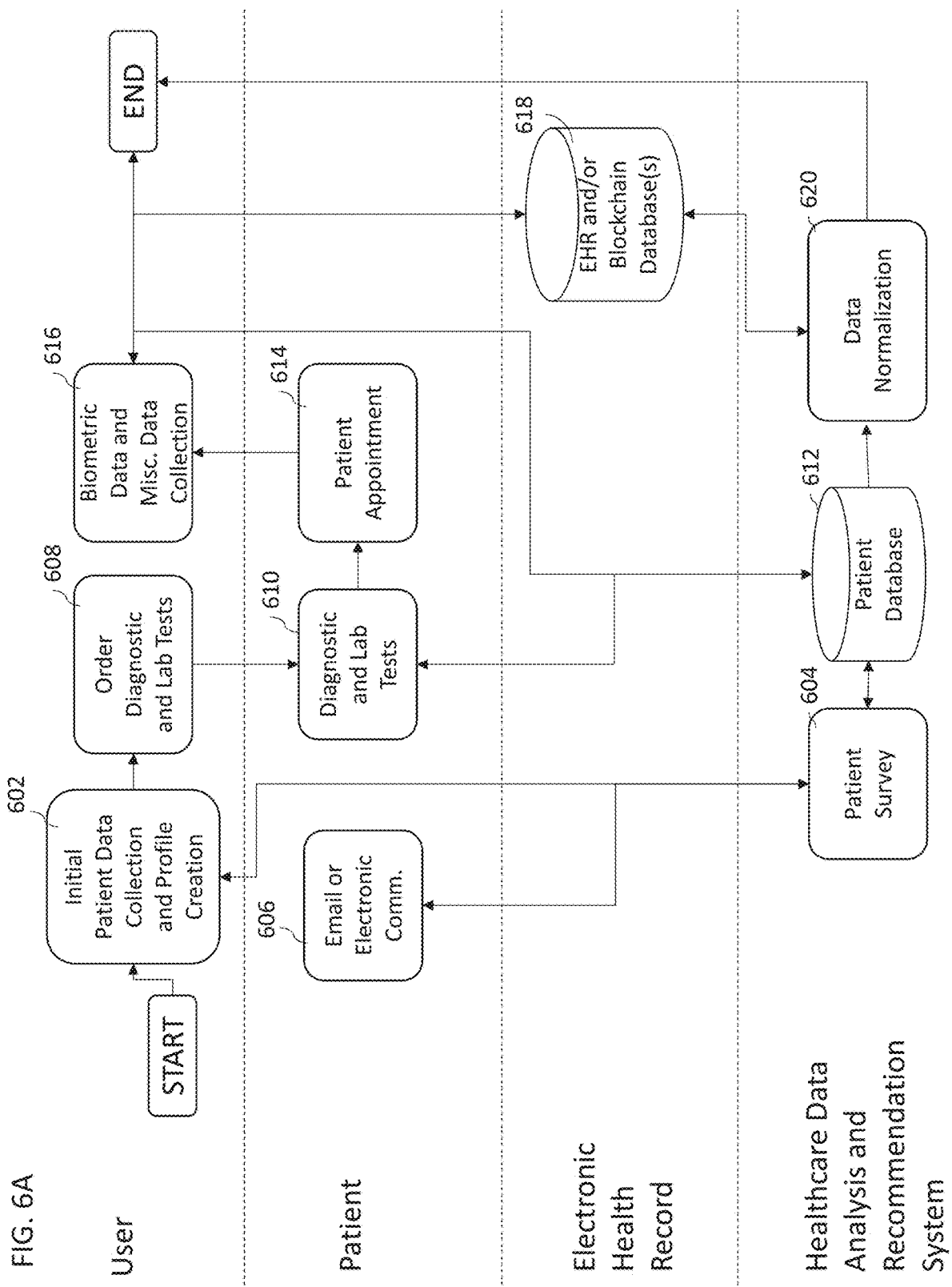
FIG. 6A illustrates a flowchart of an example end-user data collection process utilizing the healthcare data analysis and recommendation system according to various embodiments herein.

FIG. 6A illustrates a flowchart of an example end-user data collection process utilizing the healthcare data analysis and recommendation system according to various embodiments herein. In some embodiments, at 602, a patient account may be created in the healthcare data analysis and recommendation system, the patient account comprising patient biographical data such as, for example, first name, last name, date of birth (DOB) and last 4 of social security number (SSN). In some embodiments, a patient may create their own account in the healthcare data analysis and recommendation system. In some embodiments, the healthcare data analysis and recommendation system may assign patients to an affiliated healthcare provider upon account creation.

In some embodiments, additional patient data can be collected through, for example, patient surveys. In some embodiments, at 604, the patient survey can be deployed through the healthcare data analysis and recommendation system. In some embodiments, the healthcare data analysis and recommendation system can be configured to allow a patient to login via email or an activation code to complete a patient survey. In some embodiments, at 606, an email or other electronic communication can be sent automatically upon patient account creation, the email or other electronic communication containing, for example, a link to create a password or a unique activation code generated by the healthcare data analysis and recommendation system and provided to patient to log in with, for example, the activation code, name, DOB and/or last 4 digits of SSN. In some embodiments, the healthcare data analysis and recommendation system may be configured to allow a patient to complete a patient survey through a user interface within the system. In some embodiments, at 608, a health provider may obtain additional data through, for example, ordering laboratory and diagnostic testing data from an Electronic Health Record (EHR). In some embodiments, at 610, the patient may complete additional diagnostic and lab testing and the resulting data can be stored in one or more patent databases 612.

In some embodiments, the patient survey data can also be inserted into the one or more patient databases 612 and/or a healthcare data analysis and recommendation system patient chart. In some embodiments, additional patient data can be collected through an in-person appointment with a health provider at 614. In some embodiments, at 616, a health provider can collect biometric measurements and additional patient data (e.g. medications and optional ICD-10 Diagnosis codes) during the in-person appointment. In some embodiments, a health provider may manually enter biometrics into an Electronic Health Record (EHR) and/or blockchain database 618 and/or directly into the one or more patient databases 612 of the healthcare data analysis and recommendation system.

In some embodiments, the EHR database and/or blockchain database 618 can be integrated with the healthcare data analysis and recommendation system. In some embodiments, a health provider may open a patient chart in EHR and/or the healthcare data analysis and recommendation system. In some embodiments, when the healthcare data analysis and recommendation system is integrated with EHR, a healthcare provider may access the healthcare data analysis and recommendation system patient chart through a link in EHR. In some embodiments, the patient chart may open in another window with single sign-on (SSO). In some embodiments, the healthcare provider may open the healthcare data analysis and recommendation system separately from EHR. In some embodiments, patient data stored in EHR and/or blockchain database can be sent to the healthcare data analysis and recommendation system through a network interface (e.g. API, HL7, etc.). In some embodiments, patient data stored in EHR and/or blockchain database can be transferred to the one or more patient databases 612 and/or patient charts through an interface.

In some embodiments, at 620, a data collection engine of the healthcare data analysis and recommendation system may be configured to interface with the one or more patient databases 612, the EHR database and/or blockchain database 618, and one or more external databases (not shown) to collect, aggregate and normalize the patient data received from the various sources such that the data can be processed by the sophisticated functional algorithms disclosed herein (incl., for example, risk determination, condition identification, and recommendation generation algorithms).

Report/Recommendation/Plan Generation and Modification

Figure 6B:
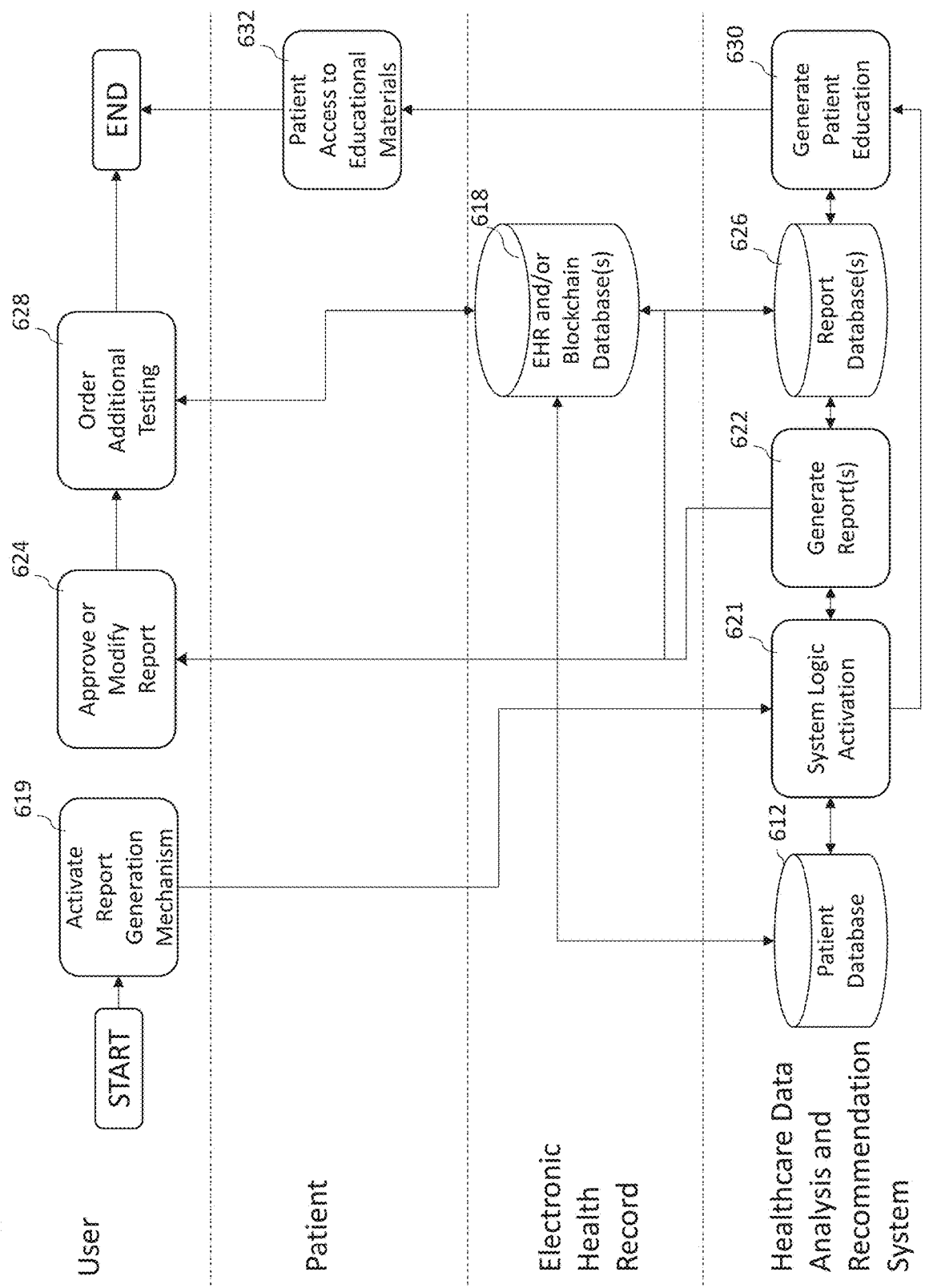
FIG. 6B illustrates a flowchart of an example report generation and modification process according to various embodiments herein.

FIG. 6B illustrates a flowchart of an example report generation and modification process according to various embodiments herein. In some embodiments, the healthcare data analysis and recommendation system comprises a report generation mechanism, which, when activated, initiates generation of a report for a user-indicated patient. For example, a health provider (or patient or other user) may, at 619, activate a report generation mechanism (e.g. selects "generate recommendations" in one or more of the user interfaces described herein). In some embodiments, at 621, activation of the report generation mechanism initiates the healthcare data analysis and recommendation system logic and sophisticated algorithms (i.e. processing engine). For example, activation may initiate one or more of the algorithms discussed in detail herein with regard to FIGS. 8A-8C, 9-15, and 18 or as shown in Appendix A). In some embodiments, the system logic determines treatment recommendations (medication, supplement, lifestyle, additional lab and diagnostic testing, etc.), risk levels or labs/diagnostics/etc., possible medical conditions to consider and identifies patient risks. In some embodiments, the system logic utilizes data from the one or more patient databases to make health determinations and generate one or more patient reports at 622. In some embodiments, the healthcare data analysis and recommendation system may have various options allowing a user to select or deselect certain logics and algorithms to be used in creating customized patient reports. For example, a user may configure the system to not perform treatment recommendation logics such that a generated report may contain relevant risk and patient condition information from which the user can develop their own recommendations. In some embodiments, system-generated recommendations and/or reports can be customized according to, for example, health clinic/provider preferences.

In some embodiments, at 624, a user (e.g. healthcare provider) may review the one or more generated reports (e.g. risk summary, treatment, lifestyle, medication, supplement, additional diagnostic and laboratory testing, etc.) and recommendations through an approval interface as described herein. In some embodiments, the user can modify and/or approve treatment recommendations through, for example, an approval interface. In some embodiments, the approved and/or modified one or more reports can be stored in one or more report databases 626 and/or the healthcare data analysis and recommendation system patient chart. In some embodiments, as part of the report modification and/or approval, a user, at 628, can order additional diagnostic or laboratory tests or specific treatment, preventative measures, and the like. In some embodiments, these additional tests, treatments, and the like can be stored in the one or more EHR databases and/or blockchain database 618, report databases 626, and/or patient databases 612.

In some embodiments, patient data can transferred into EHR and/or one or more EHR databases and/or blockchain database 618 from the healthcare data analysis and recommendation system and can be seen in appropriate places in EHR patient chart and patient encounter records.

In some embodiments, at 630, the healthcare data analysis and recommendation system logic may create patient education materials (lab results, diagnostic results, risk calculations, etc.) in addition to reports. These patient education materials may be used by patients to further understand their specific health issues and treatment plans. In some embodiments, at 632, the system may be configured to allow a patient login to access the education materials, including, for example, written, video, web links, pictorial, and pop-up materials. In some embodiments, the educational data may be displayed through a dynamic user interface configured to change over time in response to, for example, additional patient data input, individual labs and diagnostic results, completion of treatment, progress, and the like.

Updating System Logic

In some embodiments, the system logic and sophisticated algorithms may be configured to undergo an efficient update process. In some embodiments, the system logic may be updated in response to the discovery of new or improvement of existing treatments (e.g. lifestyle, medication, supplement, recommended testing, etc.), use of new lab or diagnostic tests, newly identified medical science, and the like. For example, one or more of the algorithms discussed in detail herein with regard to FIGS. 8A-8C, 9-15, and 18 or as shown in Appendix A may be updated and/or new algorithms may be added. In some embodiments, the system logic and sophisticated algorithms comprises one or more complex if-then statements. In some embodiments, in order to enable efficient system updates in response to new or changing science and/or medical developments, the healthcare data analysis and recommendation system can be configured to accept input of one or more if-then statements through, e.g., a system update interface. In some embodiments, one or more components of the system, including, e.g., the processing engine, may automatically convert and/or translate the one or more if-then statements into executable code of one or more programming languages (e.g. JSON, HTML, JAVASCRIPT, etc.).

In some embodiments, a system update interface may comprise a function type selection mechanism including, for example, options such as a general or specific risk function, condition determination, treatment recommendation, and/or the like. In some embodiments, the function type selection mechanism may be configured to allow a user to select the type of function to be updated. In some embodiments, the system update interface may be configured to allow input of, for example, additional variables to be considered in an updated function or algorithm. In some embodiments, a risk function, condition function, and/or treatment recommendation may be updated through, for example, selection of a new type or range of patient data associated with one or more risk levels, one or more conditions, and/or one or more treatments. In some embodiments, the system may be configured to transmit the user selections and inputs from the system update interface to the processing engine, wherein the processing engine may convert and/or translate the user selections and inputs into executable code of one or more programming languages (e.g. JSON, HTML, JAVASCRIPT, etc.).

For example, the system update interface may comprise one or more function drop-down menus comprising various function types to be updated. In some embodiments, a function such as a risk function may be chosen from the one or more function drop-down menus. In some embodiments, the system update interface may comprise one or more patient data type drop-down menus, wherein the patient data type drop-down menus comprise various existing or new patient data types that may be considered the selected function. For example, in some embodiments, a data type such as Total Cholesterol may be chosen from the or more patient data type drop-down menus. In some embodiments, the system update interface may also comprises one or more if-then range drop-down menus comprising patient if-then data ranges corresponding to the selected patient data type. For example, in some embodiments, various if-then ranges may be chosen, such as "if risk level: <=149 then risk is very low risk," "if risk level: 150-179 then risk is low risk," "if risk level: 180-199 then risk is moderate risk," "if risk: 200-239 then risk is high risk," "if risk level: 240-279 then risk is very high risk," and "if risk level: >=280 then risk is extremely high risk." In some embodiments, a processing engine may be configured to convert and/or translate the above selections from the one or more function, patient data type, and/or if-then range drop-down menus into executable code of one or more programming languages (e.g. JSON, HTML, JAVASCRIPT, etc.). In some embodiments, the programming language may be JAVASCRIPT.

FIG. 7 illustrates a flow chart of an example system logic update process according to various embodiments herein. In some embodiments, a new treatment, test, or the like, may be discovered, identified, or otherwise deemed useful enough to be integrated into the system logic. In some embodiments, at 702, one or more system designers (e.g. clinical team) may review the new treatment, test, or the like to determine its application and develop and define new or updated system logic and/or algorithms in plain language reflecting the scientific advances. In some embodiments, developing and defining new system logic and implementing the new logic into the system comprises updating a processing engine of the healthcare data analysis and recommendation system. In some embodiments, the processing engine and various user interfaces described herein can be configured to allow non-coders to create logic and the healthcare data analysis and recommendation system can automatically translate the plain language into executable code. In some embodiments, as part of updating the processing engine, the system may be configured to allow data definitions to be updated according to the new or updated logic. In some embodiments, updating data definitions comprises storing new functions, including the executable code and/or the plain language, in one or more of databases described herein (e.g. code databases 708, PE update databases 704, and/or RE update databases 714). In some embodiments, the system may export one or more functions to, for example, charts such as those in Appendix A, referred here as "data definitions." In some embodiments, data definitions comprise viewable spreadsheets of executable code and/or plain language explanations of the various functions and/or sophisticated algorithms of the system.

In some embodiments, the new or updated plain language processing engine logic and/or algorithms can be stored in one or more processing engine (PE) update databases 704 of the healthcare data analysis and recommendation system. In some embodiments, at 706, the healthcare data analysis and recommendation system can be configured to translate the processing engine logic into executable code that can be used to analyze and apply the system logic to patient data. In some embodiments, the executable code can be stored in one or code databases 708 of the healthcare data analysis and recommendation system. In some embodiments, at 710, the system may be configured to allow one or more system developers (e.g. development team) to test the executable processing engine code for functionality and/or accuracy.

In some embodiments, at 712, the one or more system designers may update a report engine in plain language to reflect the new treatment, test, or the like as well as the changes to the processing engine logic. In some embodiments, the report engine and the various user interfaces can be configured to allow non-coders (e.g. patients and healthcare providers) to create new reports and update existing reports. In some embodiments, the updated or new processing logic can be appended or attached to the plain language report engine update. In some embodiments, the system can be configured to enable non-coders to link processing engine logic with one or more report engine report widgets (e.g. sections and/or subsections) to allow personalization of each report per logic specific to user data. In some embodiments, similar to how the processing engine can convert and/or translate plain language functions into executable code as described above, the reporting engine can be built using widgets (e.g. sections, subsections, titles, subtitles, etc.) that are attached to risk levels, treatments, conditions, and the like from the processing engine. In some embodiments, the widgets may be static, such that the content of the widget may not be modified by logic from the processing engine, or dynamic, such that the content of the widget depends on one or more functions defined in the processing engine. In some embodiments, static widgets may include, for example, text boxes, photos, graphics, animations, and the like. In some embodiments, dynamic widgets may include, for example, dynamic text boxes, dynamic graphics, animations, photos, highlight bars, score displays, risk level displays, condition displays, treatment displays, risk factor containers, recommendation boxes, and the like, the content of which may depend on one or more functions of the processing engine. In some embodiments, the system can be configured to allow the report style, layout, and content to be customized through plain language and/or user interface mechanisms, such that coding knowledge is not required. In some embodiments, a plain language report engine update may be stored in one or more report engine (RE) update databases 714. In some embodiments, the one or more RE update databases 714 may also comprise the one or more PE update databases 704. In some embodiments, at 706, the healthcare data analysis and recommendation system can be configured to translate the report engine logic into executable code that can generate recommendations, reports, and/or education materials to be displayed to the patient through the user interface as described herein. In some embodiments, the executable code can be stored in one or code databases 708 of the healthcare data analysis and recommendation system. In some embodiments, at 710, the system may be configured to allow one or more system developers (e.g. development team) to test the executable report engine code for functionality and/or accuracy.

In some embodiments, at 716, the system comprising updated processing engine logic and report engine code can be tested with live patient data in a development and/or live environment. In some embodiments, at 718, the updated processing engine and report engine can be released for general use.

An example of the process described above may involve a new medication (e.g. Med X) that is identified as a recommended treatment option to employ. According to the example process, clinical staff may define when Med X should be recommended based upon existing data in the healthcare data analysis and recommendation system and/or new data. In some embodiments, clinical staff may create educational content for Med X and update any existing education that is effected by Med X. Clinical staff may, for example, define how this will change already existing treatments and education in the healthcare data analysis and recommendation system. Clinical staff may record the changes from the existing treatments and education in data definitions. In some embodiments, clinical staff may add new treatments and data points into the processing engine in plain language. Additionally, clinical staff may add new treatments and education to patient reports in the reports engine. The healthcare data analysis and recommendation system may automatically translate the above plain language into coded logic. In some embodiments, the development team may test the new, automatically generated logic. In some embodiments, the clinical team may test logic outputs in a developmental and/or live environment. In some embodiments, the new Med X logic may be released into a live environment.

Recommendations

Various embodiments described herein relate to generating medical recommendations based on complex logic and sophisticated algorithms incorporated in a processing engine. In some embodiments, generation of the medical recommendations comprises risk determination and/or medical condition determination. Examples of algorithms for risk determination and/or medical condition determination care shown in FIGS. 8B and 15, as well as Appendix A.

Figure 8A:
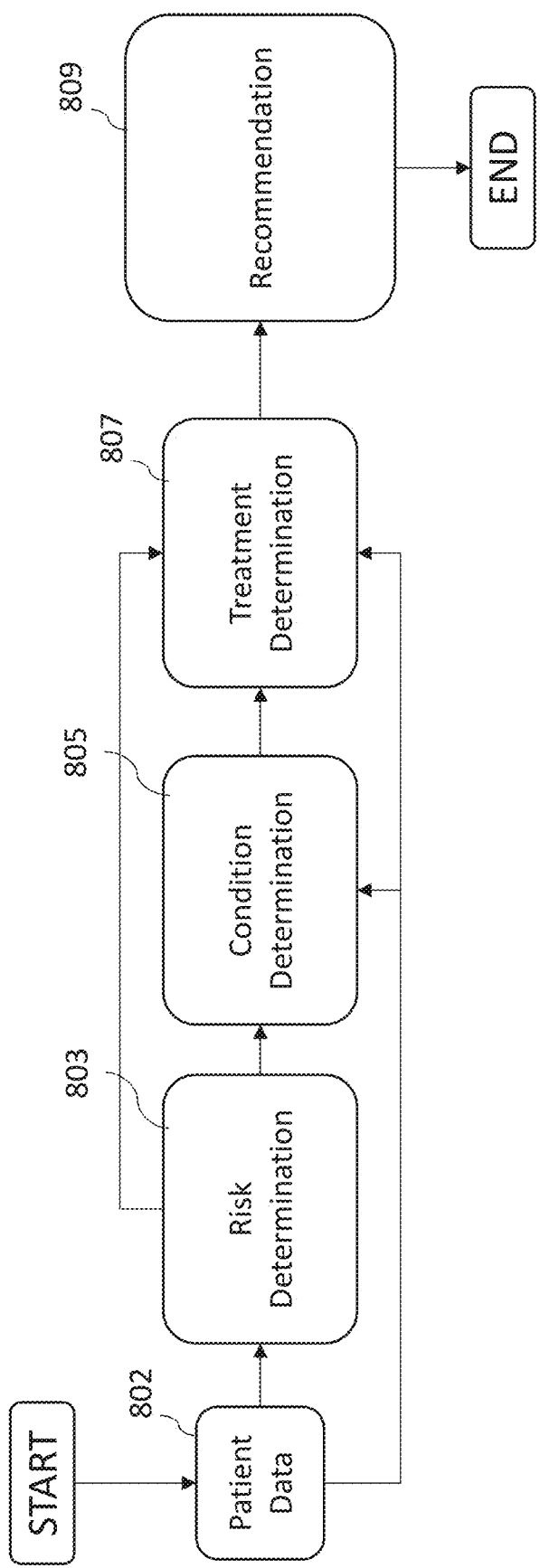
FIG. 8A illustrates a flowchart of an example recommendation generation process according to various embodiments.

FIG. 8A illustrates a flowchart of an example recommendation generation process according to various embodiments. In some embodiments, at 802, the system may collect and aggregate patient data including, for example, lab results, diagnostic results, biometrics, personal history, social history, family history, medications, lifestyle collected from vendor interfaces, manual entry, patient survey, and date of birth, among others. This may, for example, comprise implementing the process described above with reference to FIG. 6A. In some embodiments, at 803, based on patient data, the system will make various individual and aggregated risk determinations as described below, for example, as discussed with regard to FIGS. 8B, 11, 14, and 15, and as shown in Appendix A. In some embodiments, at 805, based on patient data and/or one or more risk determinations, the system may make one or more patient condition determinations comprising system determinations of whether a patient has one or more conditions, for example, as described below with reference to FIGS. 8C, 12, and 13, and shown in Appendix A. In some embodiments, at 807, based on patient data, the one or more risk determinations, and the one or more condition determinations, the system may make one or more treatment determinations comprising system determinations of whether a patient needs one or more treatments. In some embodiments, at 809, based on the treatment determinations and the patient's current treatment at the time of recommendation generation, the system may generate one or more recommendations, for example, as discussed in relation to FIG. 9 below, to be integrated into one or more patient reports by a report engine of the system.

Figure 8B:
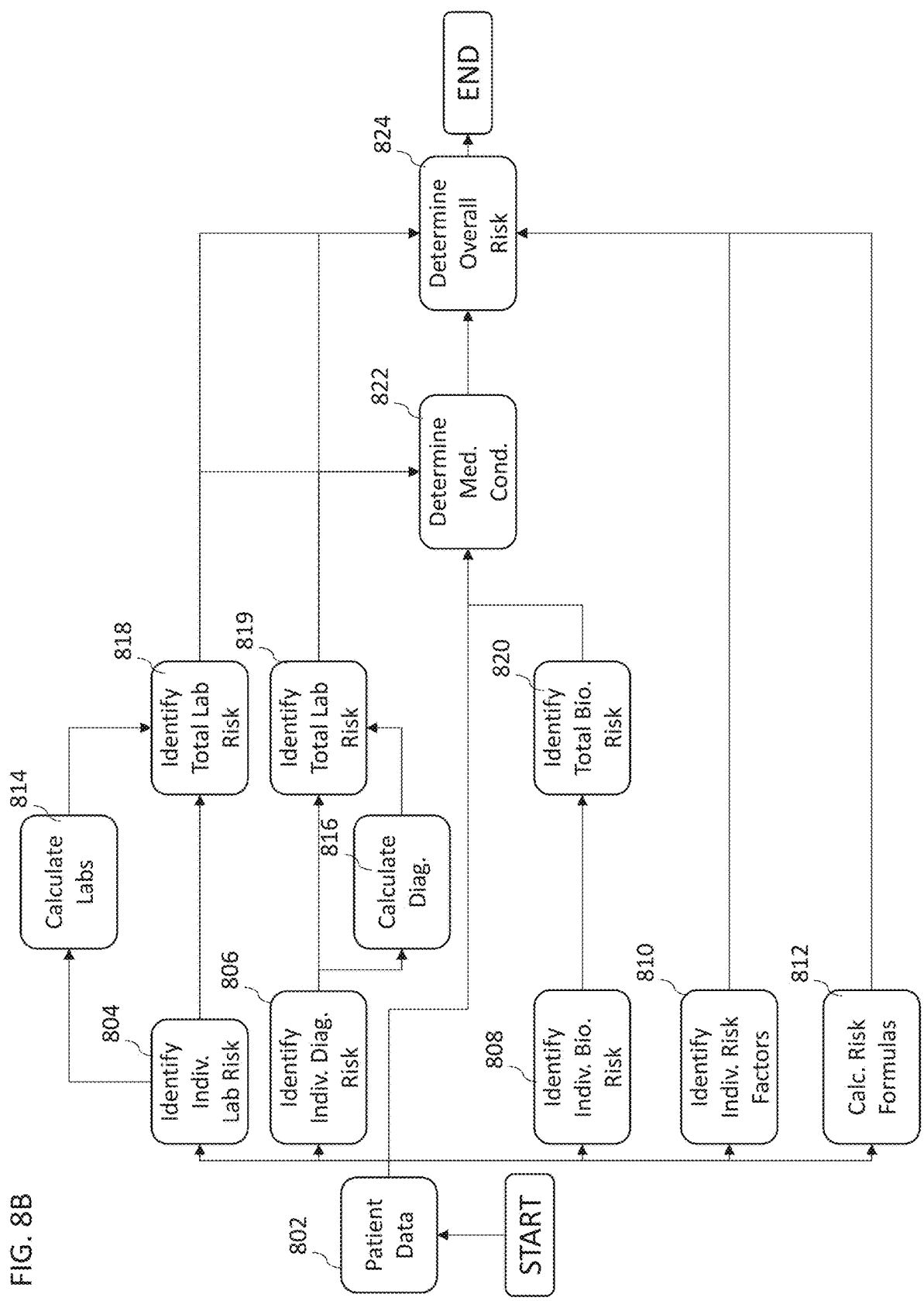
FIG. 8B illustrates a flowchart of an example risk determination logic function according to various embodiments herein.

In some embodiments, the ultimate recommendation generated by the system may be based on one or more risk determinations of the system. FIG. 8B illustrates a flowchart of an example risk determination function or algorithm according to various embodiments herein. In some embodiments, at 802, the system may collect and aggregate patient data including, for example, lab results, diagnostic results, biometrics, personal history, social history, family history, medications, lifestyle traits collected from vendor interfaces, manual entry, patient survey, and date of birth, among others, for example, as discussed with reference to FIG. 6A. In some embodiments, at 804, the system may identify a risk level of each individual lab result with respect to the condition. In some embodiments, the risk level may be determined based on one or more of the example methods for determining risk levels described herein or a like process, for example, as discussed with reference to FIGS. 8B, 11, 14, 15, and as shown in Appendix A. In some embodiments, at 806, the system may identify a risk level of each individual diagnostic result with respect to the condition. In some embodiments, the risk level may be determined based on one or more of the example methods for determining risk levels described herein or a like process, for example, as discussed with reference to FIGS. 8B, 11, 14, 15, and as shown in Appendix A. In some embodiments, at 808, the system may identify a risk level of each individual biometric result with respect to the condition. In some embodiments, the risk level may be determined based on one or more of the example methods for determining risk levels described herein or a like process, for example, as discussed with reference to FIGS. 8B, 11, 14, 15, and as shown in Appendix A.

In some embodiments, at 810, the system may identify, based on the aggregated patient data, one or more individual risk factors with respect to a condition. In some embodiments, the individual risk factors may be determined based on one or more of: personal history, social history, family history, and/or lifestyle, among others. In some embodiments, at 814, the system may calculate lab results that are obtained through formulas (e.g. LDL, nonHDL, CIMT percentile, etc.). In some embodiments, at 816, the system may calculate diagnostic results that are obtained through formulas (e.g. CIMT percentile, CIMT age, etc.). Example CIMT percentile and CIMT age formulas are described below.

Determining CIMT Percentile and Age

Percentiles for Carotid Intima-Media Thickness (CIMT) may have a relationship to cardiovascular disease. Also, the CIMT age, which is based on the median CIMT percentile across ages, may be a valuable clinical tool for convincing patients to engage in behavior change. In some embodiments, CIMT percentile and CIMT age may be beneficial data inputs for creating recommendations and reports (e.g. personalized prevention plans) according to the embodiments described herein. CIMT measurements may be standardized across vendors. However, computation of the CIMT percentile and CIMT age may be not be standardized. Some embodiments herein are directed to functions that compute CIMT percentile and CIMT age based on a person's age, sex, and CIMT.

CIMT use in clinical practice may be hindered by the absence of a formula for computing CIMT percentile. Generally, a table may be provided, comprising CIMT measurements against age and a percentile for each sex and race group. For example, see Table 1 below, which is reproduced from Howard, George, et al. "Carotid artery intimal-medial thickness distribution in general populations as evaluated by B-mode ultrasound. ARIC Investigators." Stroke 24.9 (1993): 1297-1304. This table shows percentile estimates of the CIMT measurements of the left common carotid artery across age for black females. Other tables may also include other artery segments and race/sex subgroups.

TABLE 1

Estimates of CIMT for Left Common Carotid Artery and Percentiles by Age for Black Females

|  | 45 years | 55 years | 65 years |
| --- | --- | --- | --- |
| 5th Percentile | 0.40 | 0.45 | 0.50 |
| 10th Percentile | 0.43 | 0.49 | 0.54 |
| 25th Percentile | 0.49 | 0.56 | 0.62 |
| 50th Percentile | 0.56 | 0.65 | 0.72 |
| 75th Percentile | 0.64 | 0.75 | 0.85 |
| 90th Percentile | 0.73 | 0.87 | 1.00 |
| 95th Percentile | 0.81 | 0.96 | 1.12 |

In some embodiments, in the clinical situation, the CIMT measurements may be obtained from a vendor. In some embodiments, the patient's age and sex can be obtained from a patient database, external database, and/or patient chart. In some embodiments, the system may compute an estimated CIMT percentile. In some embodiments, estimating CIMT percentile from the table requires calculation, including, for example, interpolation and/or extrapolation functions, for ages not shown, for example, ages below 45 years, ages between 45 and 55 years, ages between 55 and 65 years, and/or ages over 65 years. In some embodiments, estimating CIMT percentile from the table requires calculation, including interpolation and/or extrapolation functions, for the percentiles not shown, for example, percentiles below the $5^{th}$ percentile, percentiles between the $5^{th}$ and $10^{th}$ percentile, percentiles between the $10^{th}$ and $25^{th}$ percentile, percentiles between the $25^{th}$ and $50^{th}$ percentile, percentiles between the $50^{th}$ and $75^{th}$ percentile, percentiles between the $75^{th}$ and $90^{th}$ percentile, percentiles between the $90^{th}$ and $95^{th}$ percentile, and percentiles above the $95^{th}$ percentile.

Other studies may include results (e.g. CIMT tables) different or in addition to the results shown in Table 1, which can be used in the functions described herein to calculate CIMT percentile and/or age. However, the tables from these studies may present new problems in calculating a CIMT percentile. For example, the studies may use a different type of CIMT measurement, e.g., an average of the maximum CIMT versus the average of the average CIMT. Also, certain studies may group patients differently, for example, into age groups instead of individual ages. In some embodiments, these differences must be considered in the CIMT percentile and age calculations described herein.

Regarding CIMT age, in some embodiments, once the $50^{th}$ percentile is computed across all ages, a solution to compute the CIMT age may be based on a linear equation. In some embodiments, to estimate the CIMT for missing ages at each percentile, a linear equation may be solved for each percentile p using one or more (such as three) CIMTs obtained at each of the three ayes. In some embodiments, solving this linear equation for each percentile p may give estimates for the parameters $\beta_0$, $\beta_1$, $\beta_2$ for each of the seven percentile. In some embodiments, a total of seven sets of parameters will be given: one for each percentile. The example formula to be solved is shown below:

$$CIMT_P = \beta_0 + \beta_1 age + \beta_2 age^2$$

In some embodiments, the systems described herein can utilize this formula and the set of parameters to compute new CIMT estimates for each missing age at each of the seven percentiles.

In some embodiments, for biological reasons, it is undesirable to extrapolate estimates for an output for inputs too far from the range of inputs in the data set. Therefore, in some embodiments, CIMT for a few years before age 45 and a few years after age 65 may be extrapolated. For example, CIMT for age 40, 41, 42, 43, 44, 66, 67, 68, 69, and/or 70, and any age between two of the aforementioned values may be extrapolated. In some embodiments, extrapolation may provide CIMT estimates for ages 40 to 70 for each of the seven percentiles.

In some embodiments, the system may estimate missing CIMT percentiles for each age group. In some embodiments, to estimate the CIMT percentiles, the system may solve a non-linear equation using beta regression for each age-level using one or more CIMTs at each of the seven percentiles. In some embodiments, using beta regression ensures that the percentiles range from 0 to 100 percent. In some embodiments, solving this non-linear equation for each age-level may provide estimates for the parameters $\gamma_0$ and $\gamma_1$ for each of the 30 age-levels (i.e. age 40 to age 70). The example formula to be solved is shown below:

$$percentile_{age-level} = \frac{1}{1 + \exp(-(\gamma_0 + \gamma_1 CIMT))}$$

In some embodiments, the system may use this formula and the set of parameters to estimate the percentile for each missing percentile at each of the 30 age-levels.

In some embodiments, for ages 18 to 39, the same procedure as above can be utilized by the system, except CIMT tables can be used from more applicable studies (e.g. Stein, James H., et al. "Distribution and cross-sectional age-related increases of carotid artery intima-media thickness in young adults: the Bogalusa Heart Study." Stroke 35.12 (2004a): 2782-2787). In some embodiments, use of these tables can include using the average of the maxes for the CIMT instead of the mean of the means. In some embodiments, based on biological principles and published studies, the system can be configured to extrapolate down to age 18. In some embodiments, this step provides a set of estimates for parameters $\gamma_0$, $\gamma_1$ that can be applied to patients between ages 18 to 39 with a mean of max CIMT.

In some embodiments, for ages 71 to 95, the same procedure as above can be used by the system, instead utilizing the CIMT results from an applicable study (e.g. Stein, James H., et al. "Use of carotid ultrasound to identify subclinical vascular disease and evaluate cardiovascular disease risk: a consensus statement from the American Society of Echocardiography Carotid Intima-Media Thickness Task Force endorsed by the Society for Vascular Medicine." Journal of the American Society of Echocardiography 21.2 (2008): 93-111.). In some embodiments, however, instead of individual ages, the system may group patients by ages. In some embodiments, for ages 71-95, the CIMT may be the mean of the means. In some embodiments, this step provides a set of estimates for parameters $\gamma_0$, $\gamma_1$ that can be applied to patients between ages 71 to 95 with a mean of means CIMT.

In some embodiments, the system may create a piecewise function that uses three sets of parameters $\gamma_0$ and $\gamma_1$ to compute the CIMT percentile. For example, if ages are between 40 to 70, the set of $\gamma_0$ and $\gamma_1$ computed from a first study (e.g. Howard et al. (1993)) can be used. If ages are between 18 and 39, the set of $\gamma_0$ and $\gamma_1$ computed from a second study (e.g. Stein et al. (2004a) may be used. If ages are between 71 to 95, the patients can be grouped into one of the age groups from a third study (e.g. Stein et al. (2008)), and the set of $\gamma_0$, $\gamma_1$ computed from the third study can be used.

Regarding the computation of CIMT age, in some embodiments, from each of the first study, second study, and third study, the system may have access to the 50th percentile across the ages in those studies. In some embodiments, to estimate the age of a given CIMT, the system may solve a linear equation using the 50th percentile across the ages in each study. In some embodiments, solving this linear equation for each study may provide estimates for the parameters $\delta_0$, $\delta_1$, for each of the three studies. The example formula to be solved is shown below:

$$age = \delta_0 + \delta_1 CIMT$$

When computed from, for example, the Stein et al (2004a) study, $\delta_0$, $\delta_1$ may be computed using the mean of max CIMT. In some embodiments, the system may utilize the example formula and the set of parameters to compute CIMT age based on, for example, the CIMT and the patient's age. In some embodiments, if the patient is between ages 18 and 39, the CIMT age can be computed using a mean of max CIMT and $\delta_0$, $\delta_1$ computed from, for example, the Stein et al (2004a) study. In some embodiments, If the patient is between ages 40 and 70, the CIMT age can be computed using $\delta_0$, $\delta_1$ computed from, for example, the Howard et al. (1993) study. In some embodiments, if the patient is older than 70, the CIMT age can be computed using $\delta_0$, $\delta_1$ computed from the Stein et al. (2008) study.

In some embodiments, to compute CIMT percentile and CIMT age based on a patient's age, sex, and CIMT (either mean-mean CIMT or mean-max CIMT), the system may interpolate and extrapolate missing information and utilize a piecewise function, as described herein. The CIMT percentile and age formulas and functions provided above are exemplary in nature and the system may utilize variations of the above and/or entirely different functions to perform the computation according to various embodiments.

Recommendations (Continued)

Returning to FIG. 8B, in some embodiments, based on the individual lab risk levels determined at 804 and the calculated lab results at 814, the system may identify some or all lab results indicating a predetermined threshold level of risk with respect to the condition at 818. Similarly, based on the determined individual diagnostic risk levels at 806 and the calculated diagnostic results at 816, the system may identify some or all diagnostic results indicating a predetermined threshold level of risk with respect to the condition at 819.

In some embodiments, based on the identified risk levels of individual biometric results in 808, the system may identify one or all biometric results that indicating a predetermined threshold level of risk with respect to the condition at 820. Based on the total lab risk determination at 818, the total diagnostic risk determination at 819, and the total biometric risk determination at 820, the system may determine various medical conditions to consider by the system and/or a user at 822.

In some embodiments, at 812, the system may also calculate various risk calculation formula scores (e.g. Reynolds Risk, Framingham, ACC, scores listed in Appendix A, etc.).

In some embodiments, based on one or more of the risk calculations and risk determinations made by the system at 804, 806, 808, 810, 812, 814, 816, 818, 819, and/or 820, the system may determine an overall patient risk level at 824. In some embodiments, the overall patient risk level may be categorized as follows: Primary A, Primary B, Primary C, Secondary, and Tertiary, as shown in, for example, Appendix A. In some embodiments, individual and aggregated lab, diagnostic, biometric, and individual risk thresholds and algorithms can be found in, for example, Appendix A.

Figure 8C:
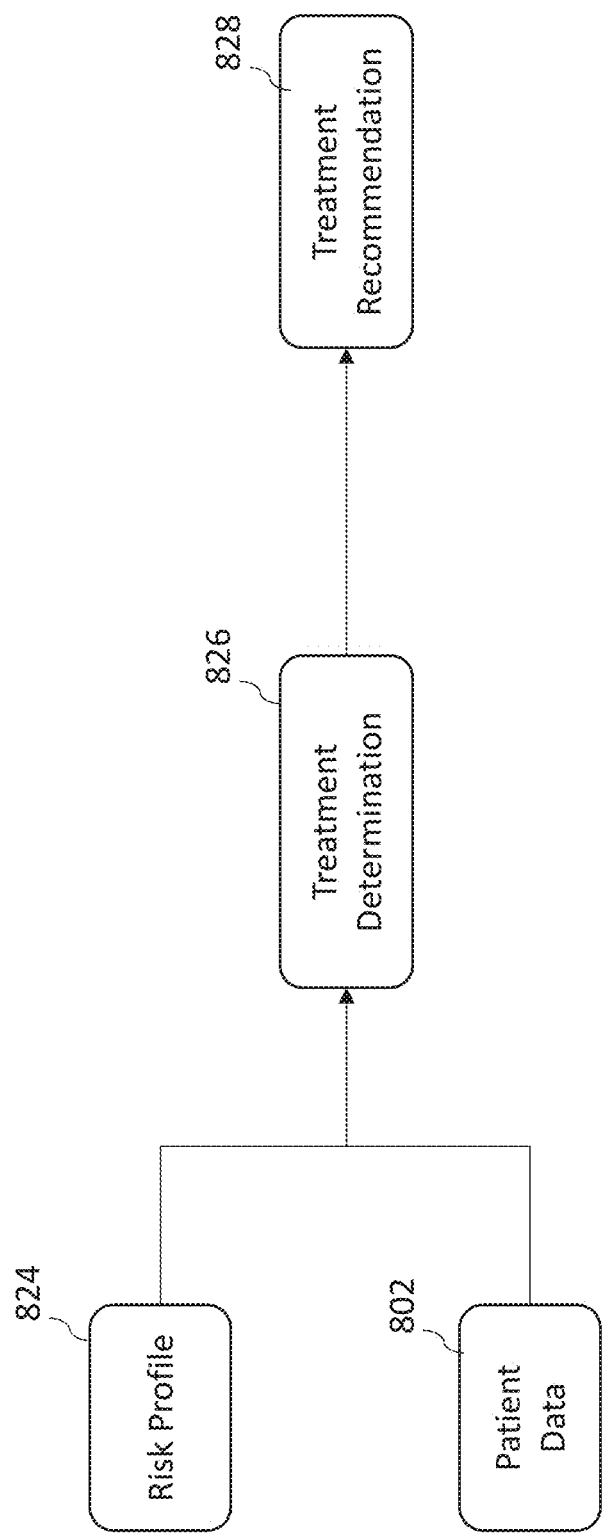
FIG. 8C illustrates a flowchart of an example recommendation logic process according to various embodiments herein.

FIG. 8C illustrates a flowchart of an example recommendation logic process according to various embodiments herein. In some embodiments, the overall determined risk level, the various medical conditions to be considered, the individual risk identifications and determinations, and/or the total risk determinations made by the system as described in FIG. 8B can comprise a patient risk profile 824. In some embodiments, based on the risk profile 824 and any other relevant patient data 802, the system may determine whether the patient needs individual treatment for one or more conditions or risks at 826 (e.g. individual medication, supplement, lifestyle, further testing, etc.). In some embodiments, based on the treatment determination, the system may develop a treatment recommendation at 828. In some embodiments, the system may consider a patient's existing treatment to generate the recommendation. For example, if the patient is already undergoing a recommended treatment when the system makes its determination, the system may recommend continuing that treatment. Alternatively, if the patient is not undergoing the generated recommended treatment at the time of generation, the system may recommend beginning treatment. Similarly, if the system determines that treatment is not necessary for a patient, but the patient is undergoing treatment at the time of recommendation generation, the system may recommend discontinuing treatment. Finally, if the patient is not undergoing treatment and the system determines that treatment is not necessary for the patient, the system may not recommend treatment.

Figure 9:
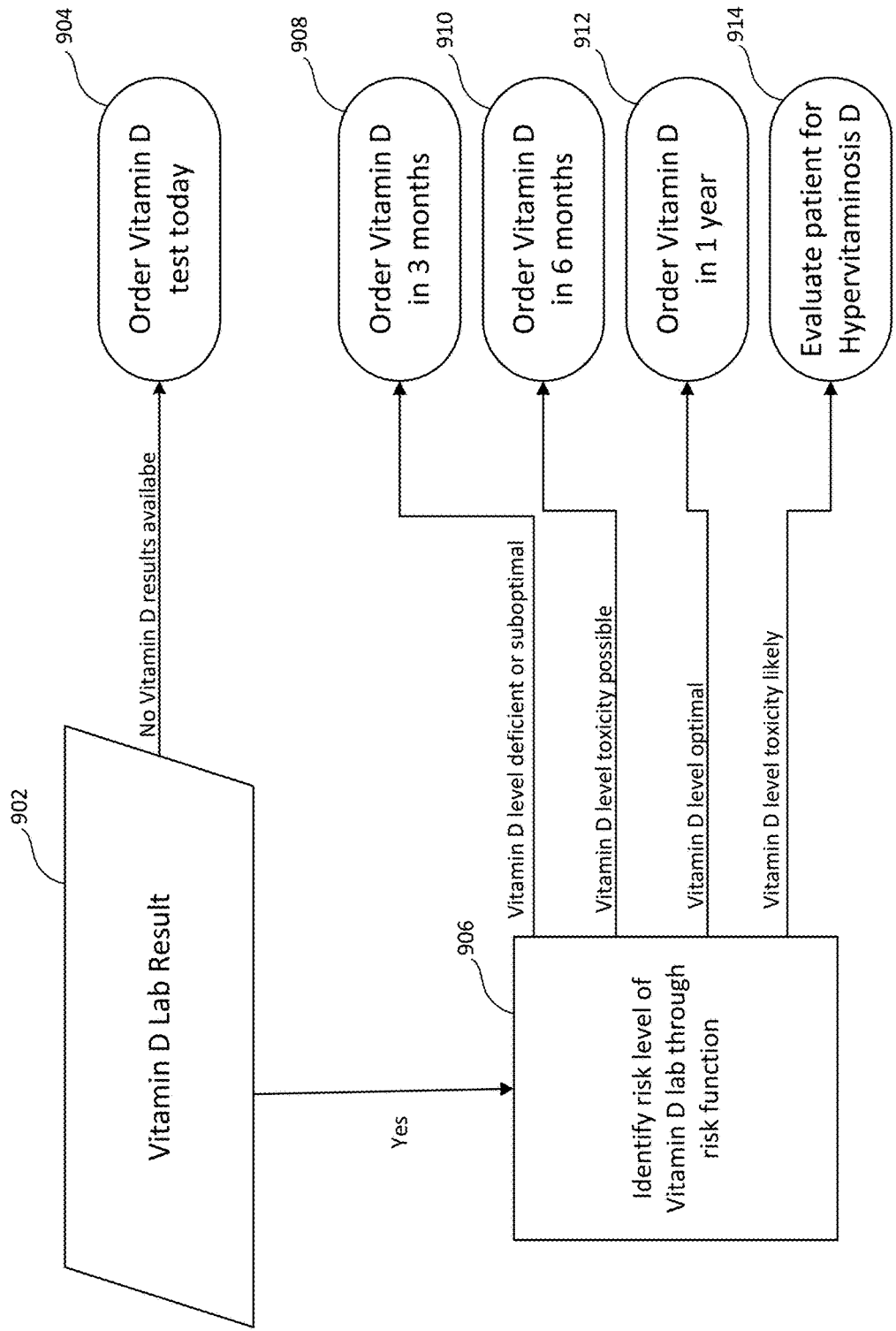
FIG. 9 illustrates a flowchart of an exemplary treatment recommendation flowchart for determining Vitamin D lab testing according to various embodiments herein.

FIG. 9 illustrates a flowchart of an exemplary treatment recommendation flowchart for determining Vitamin D lab testing according to various embodiments herein. At 902, the system can be configured to determine whether one or more Vitamin D lab results have been inputted, imported, or are otherwise available to the system. In some embodiments, at 904, if the system determines that Vitamin D lab results are not available, the system may recommend ordering lab results.

Alternatively, if the system determines that Vitamin D lab results are available at 902, the system may identify a patient risk level based on those results at 906. In some embodiments, a risk level determination may be completed according to the methods described in, for example, FIGS. 8B, 11, 14, and 15, and shown in Appendix A. In some embodiments, if the system determines that the patient's Vitamin D level is deficient or suboptimal, the processing engine may generate a recommendation to order a Vitamin D test in, for example three months at 908. In some embodiments, if the processing engine's risk function determines that the patient may have possible Vitamin D toxicity, the system may generate a recommendation to order a Vitamin D test in, for example, six months 910. In some embodiments, if the processing engine's risk function determines that the patient has optimal Vitamin D levels, the system may generate a recommendation to order a Vitamin D test in, for example, one year at 912. In some embodiments, if the processing engine's risk function determines that the patient has likely toxic Vitamin D levels, the system may generate a recommendation to evaluate the patient for hypervitaminosis at 914. The recommendations described herein are examples and any treatments, supplementations, medications, diet plans, exercise plans, and the like may be generated based on the system condition and risk function determinations. Example recommendation and report formulas can be found in Appendix A.

Figure 10:
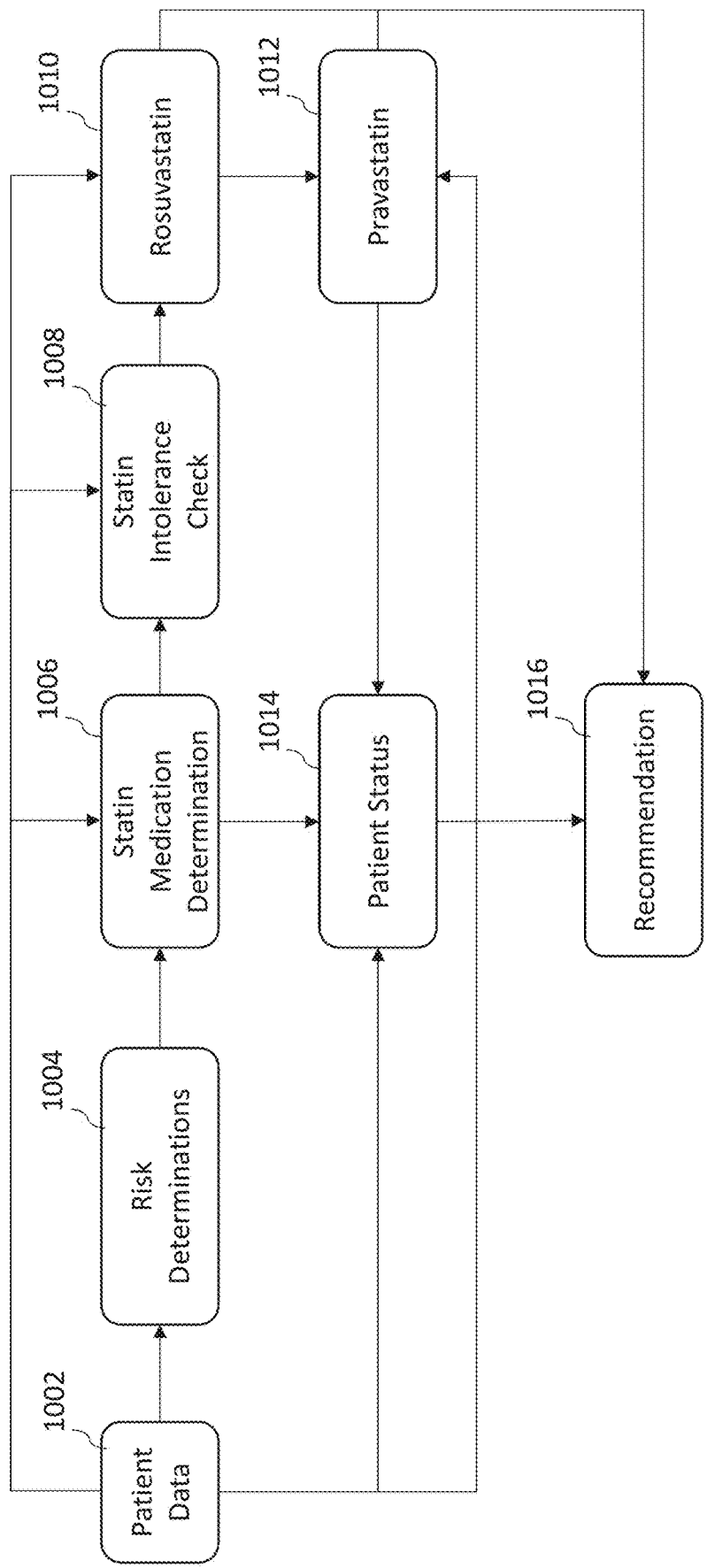
FIG. 10 illustrates a flowchart of an exemplary treatment recommendation flowchart for determining statin medications according to various embodiments herein.

FIG. 10 illustrates a flowchart of an exemplary treatment recommendation flowchart for determining statin medications according to various embodiments herein. In some embodiments, at 1002, the system may collect and aggregate patient data including, for example, lab results, diagnostic results, biometrics, personal history, social history, family history, medications, lifestyle traits collected from vendor interfaces, manual entry, patient survey, and date of birth, among others. In some embodiments, at 1004, the system may make one or more individual and aggregate risk determinations using, for example, the methods described in FIG. 8B. In some embodiments, at 1006, based on patient data and the risk determinations, the system may determine whether a patient needs a statin medication (i.e. treatment determination). In some embodiments, the treatment recommendation may be completed using treatment specific logic (e.g. treatment specific risk thresholds).

In some embodiments, if the system determines that the patient does not need a statin medication at 1006, the system may review, for example, patient data, to determine whether the patient is currently taking statin medication at 1014. In some embodiments, if the patient is currently taking a statin medication, the system may generate a recommendation to discontinue or continue taking the medication at 1016.

Alternatively, in some embodiments, if the system determines that the patient requires a statin medication at 1006, the system may review, for example, whether the patient has a statin intolerance 1008 and/or determine whether the patient is currently taking statin medication at 1014. In some embodiments, the statin intolerance determination may be completed using specific tolerance logic. In some embodiments, if the system determines that the patient is intolerant to statin, the system may recommend a retrial of Rosuvastatin.

In some embodiments, at 1010, the system may determine whether a patient needs Rosuvastatin based on the statin intolerance determination at 1008 and the statin medication determination at 1006. In some embodiments, the determination at 1010 comprises a separate treatment determination than the statin treatment determination at 1006 and may comprise separate logic. Based on the Rosuvastatin determination at 1010, the system may either generate a recommendation to prescribe Rosuvastatin at 1016 (if Rosuvastatin needed) or perform another treatment determination (i.e. separate logic) to determine if the patient needs Pravastatin at 1012 (if Rosuvastatin not needed). In some embodiments, if the system determines that the patient needs Pravastatin, the system may recommend prescribing Pravastatin at 1016. If, instead, the system determines that the patient does not need either Rosuvastatin or Pravastatin, the system may determine whether the patient is currently taking statin medication at 1014 and recommend that the patient continue or discontinue taking statin medication at 1016. Alternatively, if the patient is not currently taking statin medication, the system may not recommend prescribing statin medication at 1016. FIGS. 9 and 10 are exemplary recommendation function algorithms as described herein and not meant to be limit the disclosure herein. Other recommendation function algorithms may also be implemented, including, for example, those shown in Appendix A.

Condition Identification

Figure 11:
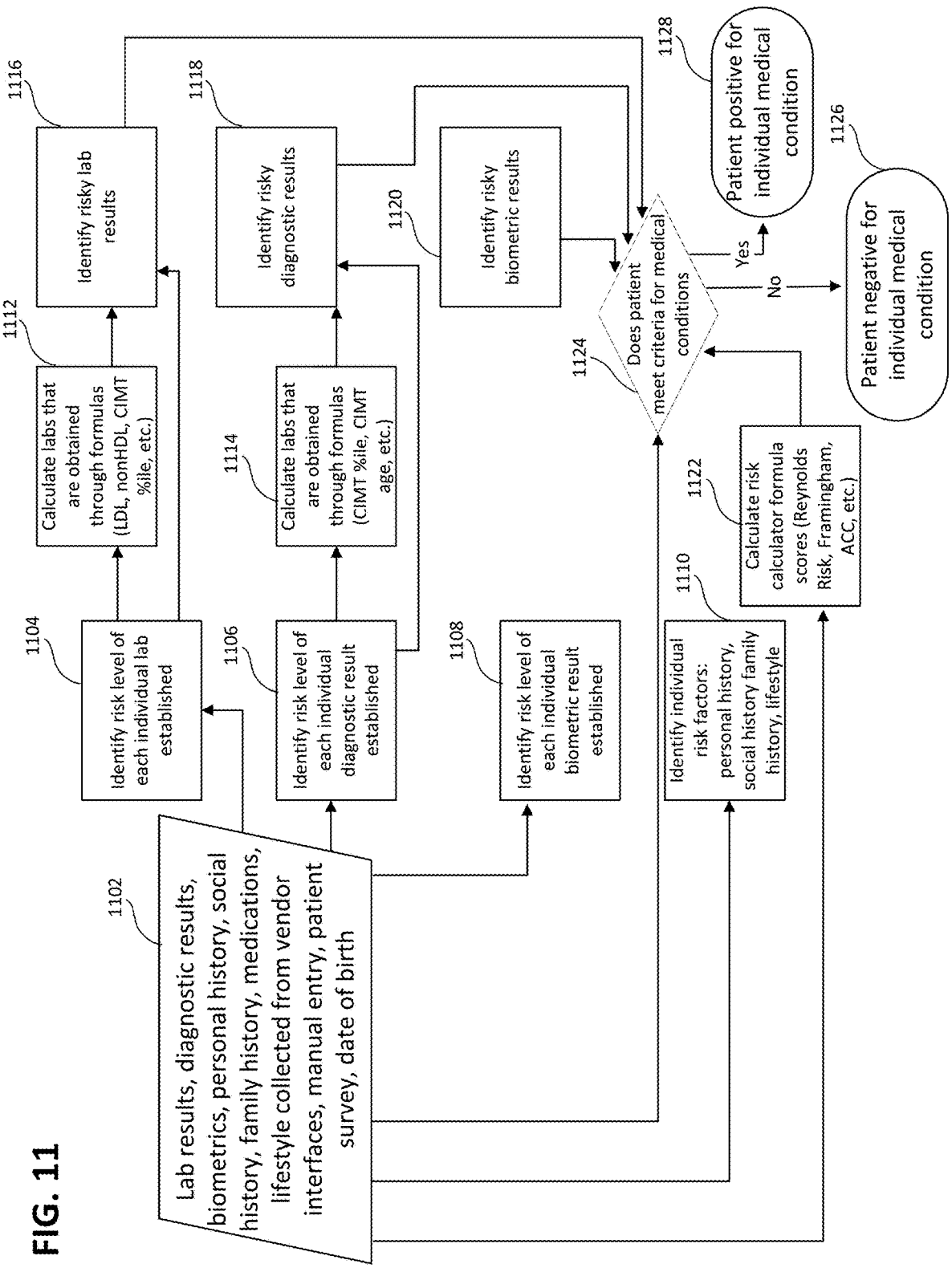
FIG. 11 illustrates a flowchart of an example condition identification process according to various embodiments herein.

In some embodiments, generating a recommendation may require the processing engine to determine whether the patient is positive or negative for a given individual condition. In some embodiments, the system's recommendation, to be integrated into one or more patient reports by the reporting engine, may be based on one or more condition determinations. FIG. 11 illustrates a flowchart of an example condition identification process according to various embodiments herein. In some embodiments, the example method illustrated in FIG. 11 can be used to determine if a patient is positive or negative for a condition and can determine the patient's risk with respect to the given condition. In some embodiments, the example methods illustrated in FIG. 11 can be completed by a processing engine as described herein. Based on the results of the example method, a reporting engine may generate one or more reports containing risk determinations, treatment recommendations, and educational materials, among others to inform the patient about his/her condition and medical options. In some embodiments, at 1102, the system may collect and aggregate patient data including, for example, lab results, diagnostic results, biometrics, personal history, social history, family history, medications, lifestyle habits collected from vendor interfaces, manual entry, patient survey, and date of birth, among others. In some embodiments, at 1104, the system may identify a risk level of each individual lab result with respect to the condition. In some embodiments, the risk level may be determined based on one or more of the example methods for determining risk levels described herein or a like process. In some embodiments, at 1106, the system may identify a risk level of each individual diagnostic result with respect to the condition. In some embodiments, the risk level may be determined based on one or more of the example methods for determining risk levels described herein or a like process. In some embodiments, at 1108, the system may identify a risk level of each individual biometric result with respect to the condition. In some embodiments, the risk level may be determined based on one or more of the example methods for determining risk levels described herein or a like process. For example, the risk level may be determined based on the methods described in FIGS. 8B, 11, 14-15, and Appendix A.

In some embodiments, at 1110, the system may identify, based on the aggregated patient data, one or more individual risk factors with respect to the condition. In some embodiments, the individual risk factors may be determined based on one or more of: personal history, social history, family history, and/or lifestyle, among others. In some embodiments, at 1112, the system may calculate lab results that are obtained through formulas (e.g. LDL, nonHDL, CIMT percentile, etc.). In some embodiments, at 1114, the system may calculate diagnostic results that are obtained through formulas (e.g. CIMT percentile, CIMT age, etc.).

In some embodiments, based on the individual lab risk levels determined at 1104 and the calculated lab results at 1112, the system may identify some or all lab results indicating a predetermined threshold level of risk with respect to the condition at 1116. Similarly, based on the determined individual diagnostic risk levels at 1106 and the calculated diagnostic results at 1114, the system may identify some or all diagnostic results indicating a predetermined threshold level of risk with respect to the condition at 1118. In some embodiments, based on the identified risk levels of individual biometric results in 1108, the system may identify one or all biometric results that indicating a predetermined threshold level of risk with respect to the condition at 1120.

In some embodiments, at 1122, the system may also calculate various risk calculation formula scores (e.g. Reynolds Risk, Framingham, ACC, etc.). In some embodiments, based on one or more of the risk identifications in 1116, 1118, 1120, and 1122, the system may determine whether the patient meets predetermined criteria for the medical condition at 1124. In some embodiments, if the patient meets the predetermined criteria, the patient may be determined to be positive for the individual medical condition 1128. Alternatively, if the patient does not meet the predetermined criteria, the system may determine that the patient is negative for the individual medical condition at 1126. Based on this final determination, the report engine of the system may generate one or more reports, recommendations, plans, educational materials, and the like describing the patient's condition and their health options to be displayed through a dynamic user interface to the patient. Example condition identification function algorithms can be found in Appendix A.

Figure 12:
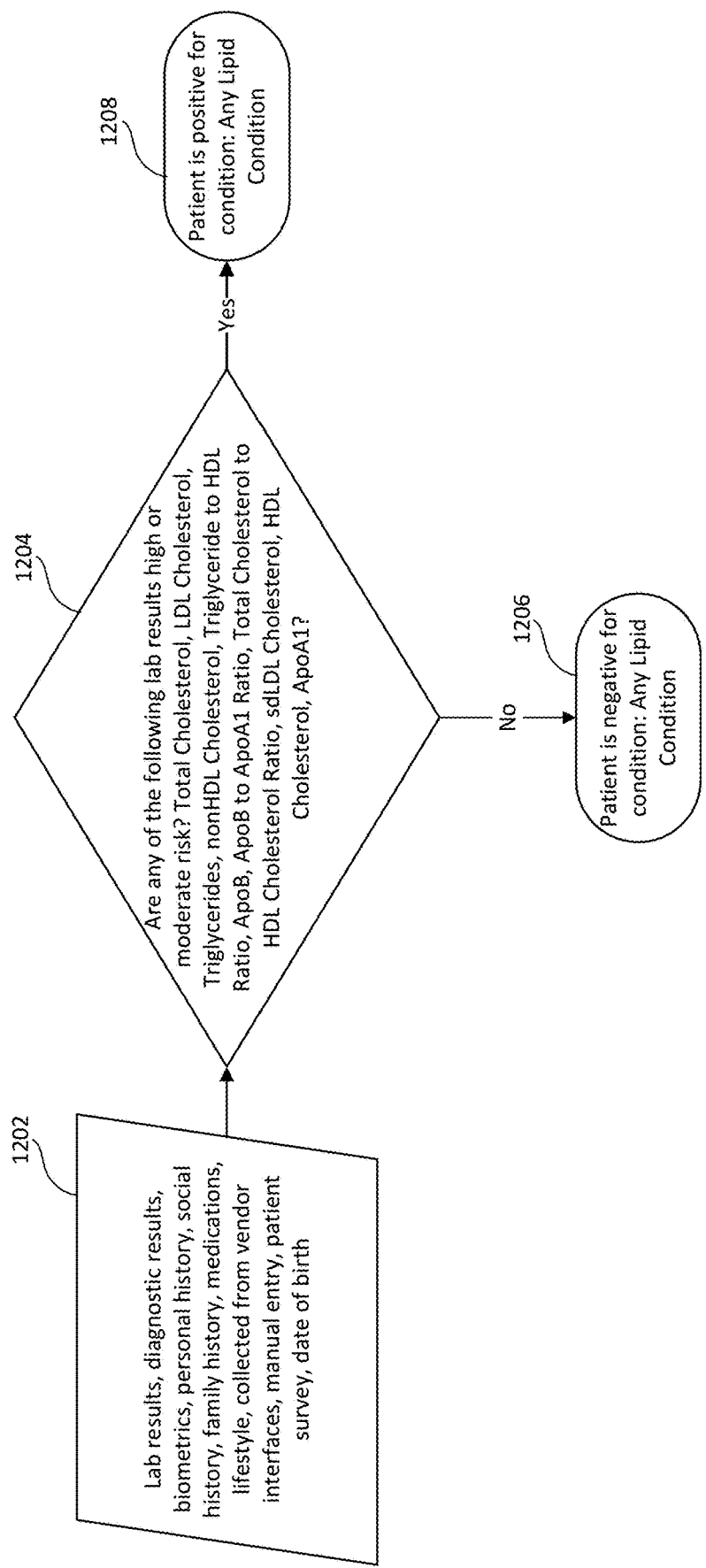
FIG. 12 illustrates a flowchart of an exemplary lipid condition identification process according to various embodiments herein.

FIG. 12 illustrates a flowchart of an exemplary lipid condition identification process according to various embodiments herein. In some embodiments, the system may utilize this logic to determine whether the patient has any lipid condition. In some embodiments, at 1202, the system may collect and aggregate patient data including, for example, lab results, diagnostic results, biometrics, personal history, social history, family history, medications, lifestyle collected from vendor interfaces, manual entry, patient survey, and date of birth, among others. In some embodiments, at 1204, the system may determine if any of the following lab results indicate that the patient is at a moderate or high risk of having a lipid condition: total cholesterol, LDL Cholesterol, triglycerides, nonHDL cholesterol, triglyceride to HDL Ratio, ApoB, ApoB to ApoA1 Ratio, total cholesterol to HDL cholesterol ratio, sdLDL cholesterol, HDL cholesterol, and/or ApoA1, among others. In some embodiments, if the system, based on the patient data, determines that the patient is positive for any of the above conditions, the system may determine that the patient is positive for a lipid condition at 1208. Alternatively, if the system determines that the patient is negative for all of the above conditions, the system may determine that the patient is negative for a lipid condition at 1206.

In some embodiments, based on the determinations regarding the condition of the patient, the processing engine may generate a recommendation, such as prescribing or adjusting medications, implementing diet or exercise plans, recommending treatment, or the like. In some embodiments, the report engine may generate one or more reports containing the risk determinations, treatment recommendations, and educational materials to inform the patient about his/her condition and health options.

Figure 13:
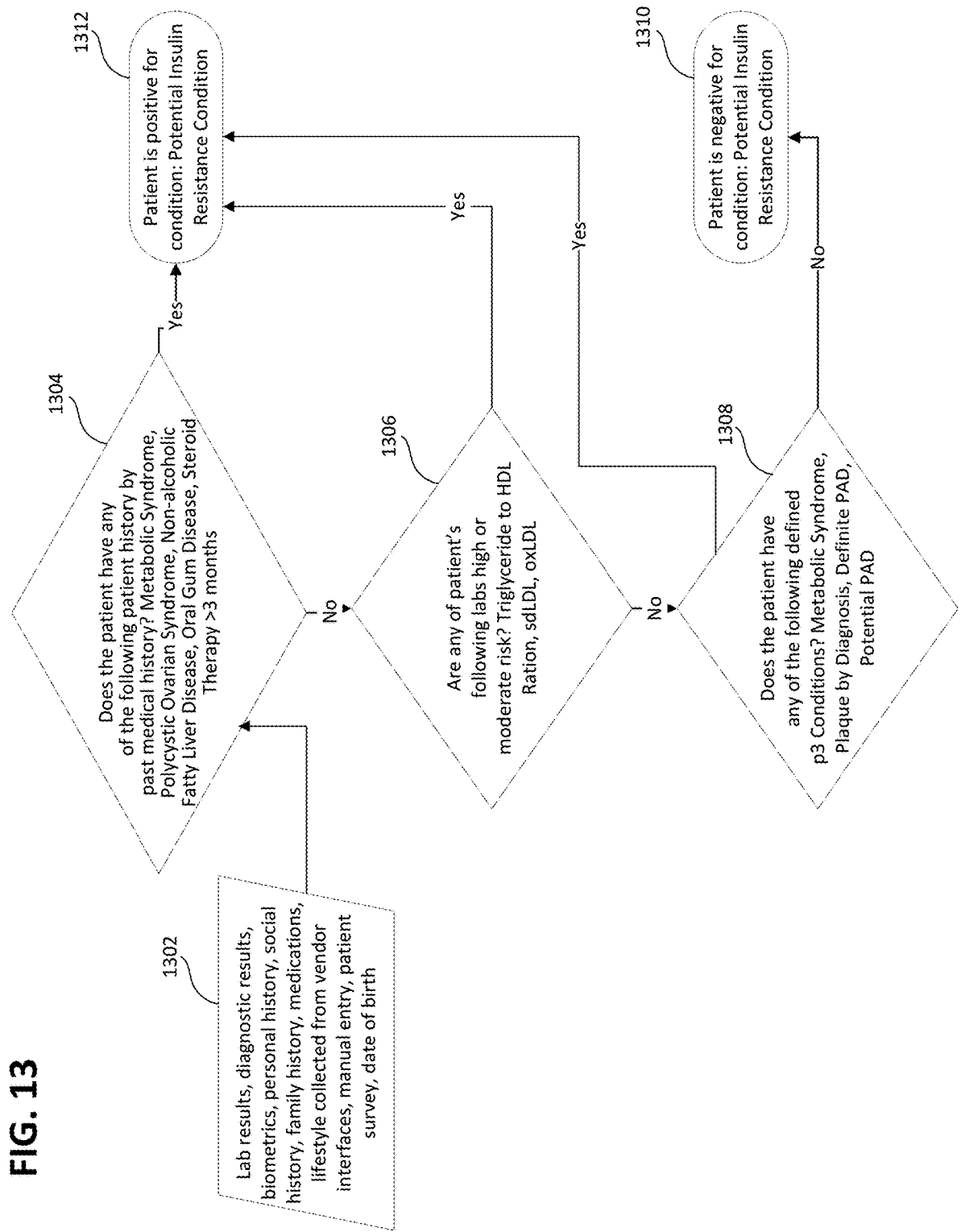
FIG. 13 illustrates a flowchart of an exemplary insulin resistance condition identification flowchart according to various embodiments herein.

FIG. 13 illustrates a flowchart of an exemplary potential insulin resistance condition identification flowchart according to various embodiments herein. In some embodiments, the system may utilize this logic to determine whether the patient has a potential insulin resistance condition. In some embodiments, at 1302, the system may collect and aggregate patient data including, for example, lab results, diagnostic results, biometrics, personal history, social history, family history, medications, lifestyle collected from vendor interfaces, manual entry, patient survey, and date of birth, among others. In some embodiments, at 1304, the system may utilize the patient data to determine, for example, if the patient has had any of the following conditions in their past medical history: metabolic syndrome, polycystic ovarian syndrome, non-alcoholic fatty liver disease, oral gum disease, or if the patient has undergone steroid therapy for more than three months. If the system determines that the patient that one of the above conditions are met, the system may determine that the patient has a potential insulin resistance condition at 1312.

Alternatively, if, at 1304, the system determines one of the above conditions is not met, the system may cross-check a risk determination at 1306. For example, the system may cross-check a system determination of whether the patient, based on patient data such a lab results, has a moderate or high risk of disease. In some embodiments, the system may check risk based on triglyceride to HDL Ration, sdLDL, and/or oxLDL, among others. In some embodiments, the system may assess risk according to one or more of the example risk determination methods described herein or similar methods based on other specific patient data. If the system determines that the patient is at moderate or high risk at 1306, the system may determine that the patient has a potential insulin resistance condition at 1312.

Alternatively, if, at 1306, the system determines that the patient is not at moderate or high risk, the system may cross-check a condition determination at 1308. For example, the system may cross-check a system determination of whether the patient, based on patient data available to the system has any of the following conditions: metabolic syndrome, plaque by diagnosis, definite PAD, and/or potential PAD, among others. In some embodiments, the system may determine patient condition according to one or more of the example condition determination methods described herein or similar methods based on other specific patient data. If the system determines that the patient has one of the above conditions at 1308, the system may determine that the patient has a potential insulin resistance condition at 1312.

In some embodiments, if the system does not identify alarming patient history at 1304, does not make a moderate or high risk determination at 1306, and/or does not make a identify a positive patient condition at 1308, the system may determine that the patient does not have a potential insulin resistance condition at 1310.

In some embodiments, based on the determinations regarding the condition of the patient, the processing engine may generate a recommendation, such as prescribing or adjusting medications, implementing diet or exercise plans, recommending treatment, or the like. In some embodiments, the report engine may generate one or more reports containing the risk determinations, treatment recommendations, and educational materials to inform the patient about his/her condition and health options.

Risk Identification

Figure 14:
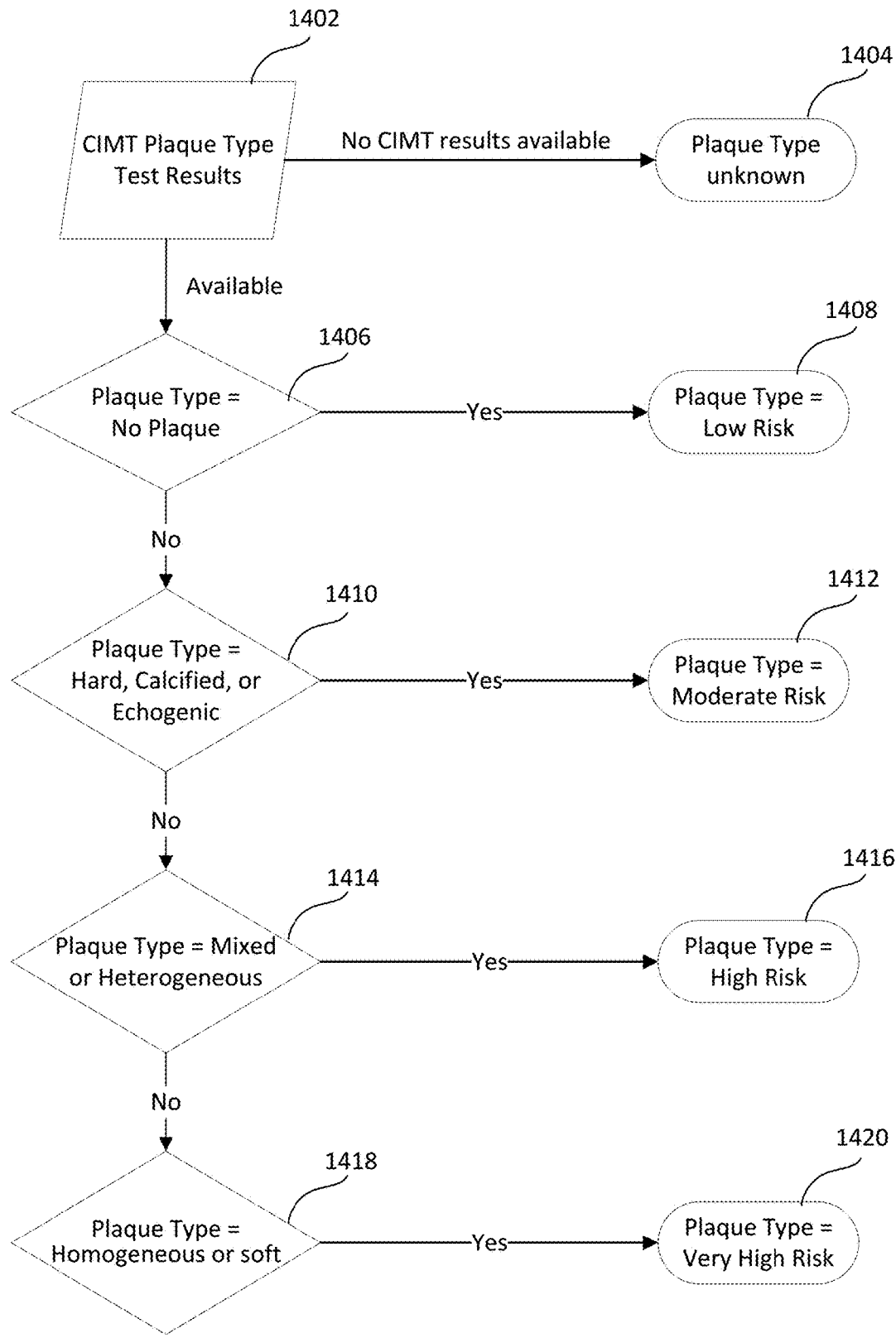
FIG. 14 illustrates a flowchart of an exemplary risk identification process for determining health risk based on atheromatous plaque type according to various embodiments herein.

In some embodiments, determining whether a patient is positive or negative for a condition may require a risk determination to be made by the processing engine of the system based on, for example, patient data entered into the system through the user interfaces described above. FIG. 14 illustrates a flowchart of an exemplary risk identification process for determining health risk based on atheromatous plaque type according to various embodiments herein.

In some embodiments, at 1402, the system may determine if CIMT Plaque Type test results data has been inputted, imported or otherwise available. In some embodiments, at 1404, if no CIMT results are available, the plaque type may be unknown. In some embodiments, if no test results are available the system may recommend ordering testing. In some embodiments, if there are test results that indicate no plaque is present at 1406, the system may determine at 1408 that the patient is at low risk of heart disease, heart attack, or other diseases. In some embodiments, if there are test results that indicate there is hard, calcified or echogenic plaque present at 1410, the system may determine at 1412 that the patient is at moderate risk of heart disease, heart attack, or other diseases. In some embodiments, if there are test results that indicate mixed or heterogeneous plaque is present at 1414, the system may determine at 1416 that the patient is at high risk of heart disease, heart attack, or other diseases. In some embodiments, if there are test results that indicate homogeneous or soft plaque is present at 1418, the system may determine at 1420 that the patient is at very high risk of heart disease, heart attack, or other diseases.

In some embodiments, based on the determinations regarding the risks of patient's plaque type, the processing engine may generate a recommendation, such as prescribing or adjusting medications that lower blood pressure and cholesterol, as well as provide nutrition and lifestyle recommendations. In some embodiments, the report engine may generate one or more reports containing the risk determinations, treatment recommendations, and educational materials to inform the patient about his/her condition and health options.

Figure 15:
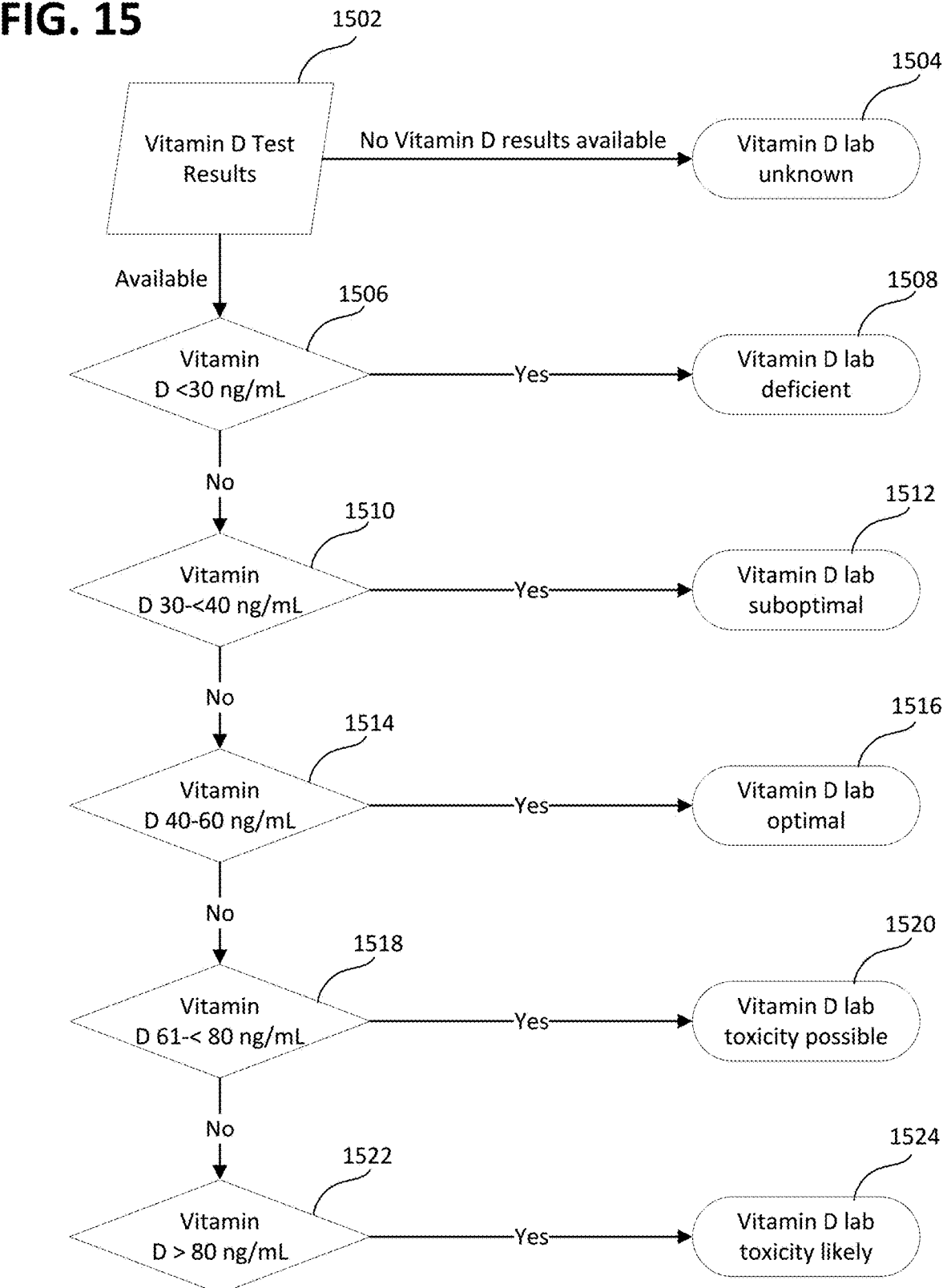
FIG. 15 illustrates a flowchart of an exemplary risk identification process for determining Vitamin D deficiency or toxicity according to various embodiments herein.

FIG. 15 illustrates a flowchart of an exemplary risk identification process for determining Vitamin D deficiency or toxicity according to various embodiments herein. In some embodiments, at 1502, the system may determine whether Vitamin D test results or data has been inputted, imported, or otherwise available to the system. If there are no test results or insufficient data available, at 1504, the system may determine that a patient's Vitamin D level is unknown and may, for example, recommend that the patient undergo Vitamin D tests. If Vitamin D test result data is available to the system, the processing engine of the system may access the Vitamin D levels in the patient at 1506, 1510, 1514, 1518 and 1522. If, at 1506, the patient's Vitamin D level is less than 30 ng/ml, the system may determine that the patient is Vitamin D deficient at 1508. Alternatively, if, at 1510, the patient's Vitamin D level is between 30 and 40 ng/ml, the system may determine that the patient's Vitamin D level is suboptimal at 1512. If, at 1514, the patient's Vitamin D level is between 40 and 60 ng/ml, the system may determine that the patient's Vitamin D is optimal at 1516. If, at 1518, the patient's Vitamin D level is between 61 and 80 ng/ml, the system may determine that the patient's Vitamin D level is potentially or possibly toxic at 1520. If, at 1522, the patient's Vitamin D level is greater than 80 ng/ml, the system may determine that the patient's vitamin level is likely toxic at 1524.

In some embodiments, based on the determinations regarding the risks of patient's Vitamin D levels, the processing engine may generate a recommendation, such as Vitamin D supplementation. In some embodiments, the report engine may generate one or more reports containing the risk determinations, treatment recommendations, and educational materials to inform the patient about his/her condition and health options.

The embodiments described above are exemplary in nature and are not meant to be limiting. Other example risk identification functions and/or algorithms can be found, for example, in Appendix A.

Healthcare Data Analysis and Recommendation System

Figure 16:
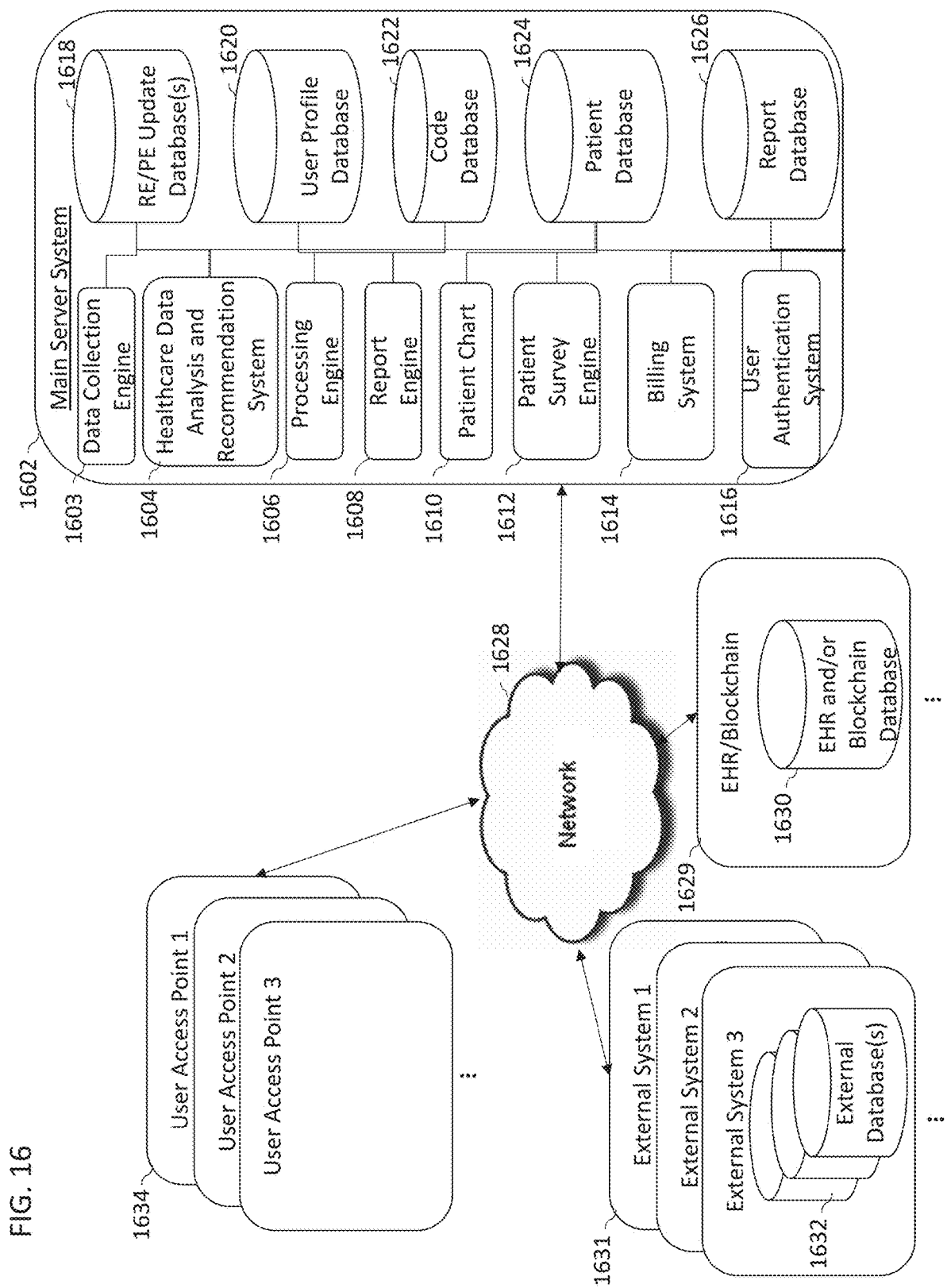
FIG. 16 illustrates a schematic diagram of a healthcare data analysis and recommendation system according to various embodiments described herein.

FIG. 16 is a schematic diagram illustrating a healthcare data analysis and recommendation system according to various embodiments. In some embodiments, a main server system 1602 can comprise a data collection engine 1603, a healthcare data analysis and recommendation system 1604, a processing engine 1606, a report engine 1608, a data entry interface or patient chart 1610, a patient survey engine 1612, a billing system 1614, a user authentication system 1616, one or more RE/PE update databases 1618, a user profile database 1620, a code database 1622, a patient database 1624, and/or a report database 1626. The main server system can be connected to a network 1628. The network can be configured to connect the main server to one or more EHR systems and/or blockchain platforms 1629 comprising one or more EHR databases and/or blockchain databases 1630, one or more other external systems 1631 comprising one or more external databases 1632, and/or one or more user access point systems 1634.

In some embodiments, the data collection engine 1603 can be configured to receive, aggregate, and normalize patient data from one or more data entry interfaces, patient charts, data importations, external databases (incl. EHR databases and/or blockchain databases), data received through utilization of an API, or otherwise. The healthcare data analysis and recommendation system 1604 can be configured to efficiently provide sophisticated health data processing and treatment recommendations. The processing engine 1606 can be configured to interface with a plurality of medical data sources (e.g. patient database 1624, EHR database and/or blockchain databases 1630, external databases 1632), wherein one or more medical data sources of the plurality of medical data sources comprises medical data having an incongruent data structure to another medical data source of the plurality of medical data sources, and wherein the medical data comprises one or more medical data types. In some embodiments, the processing engine may also be configured to normalize the aggregated medical data into an operational data structure, perform an adaptive rule-based analysis of the normalized medical data to identify a patient medical risk level, wherein the rule-based analysis comprises both collectively and individually evaluating each medical data type of the normalized medical data, and develop one or more patient treatment recommendations and/or treatment regimens based on the identified patient medical risk level.

The report or reporting engine 1608 may be configured to generate a dynamic patient health reporting interface and update the dynamic patient health reporting interface in response to a user input. The report engine 1608 may be further configured to generate the dynamic patient health reporting interface comprising a visual representation of the patient medical risk level and/or the one or more patient treatment recommendations and/or treatment regimens.

The data entry interface or patient chart 1610 can be configured to allow input of patient data and to verify information associated with the user (for example, information inputted by the user, retrieved information based on a user's IP address, and/or the like). In some embodiments, the patient survey engine 1612 may be configured to deploy a patient survey through, for example, the data entry interface or patient chart 1610. In some embodiments, the billing system 1614 can be configured to charge users for various provided services using any available payment methods. In some embodiments, the user authentication system 1616 may generate unique activation codes for user activation and may authenticate user logins and data entry.

The main server system 1602 and/or the healthcare data analysis and recommendation system 1604 can perform the steps of processing, storing, generating, transmitting, and receiving on a remote server instead of performing such processing on the client device. As such, processing can be offloaded to a remote server, storage of the computations, results, and input needed for the results can be stored on the server rather than on the client device, and the required throughput can be reduced based (for example, the results can be sent instead of all inputs needed to determine the result to the client device).

The one or more RE/PE Update databases 1618 can store and provide one or more plain language updates to the processing engine and report engine. The user profile database 1620 may store and provide a collection of user profiles associated with patients comprising biographical information. The code database 1622 may store and provide the system generated executable code. The patient database 1624 may store and provide the various patient health data inputted or imported into the system. The report database 1626 may store and provide the generated patient reports, recommendations, risk assessments, condition assessments, plans, and the like.

In some embodiments, the healthcare data analysis and recommendation system can comprise an indication of one or more users' user access point 1634 and IP address or browser cookie information.

The network 1628 can allow the main server system 1602 to exchange data with one or more external databases 1632, EHR database and/or blockchain databases 1630, and one or more user access points 1634. The EHR database and/or blockchain database 1630 may store and provide, through the network, patient health data, including diagnostic and laboratory test results. The user access points 1634 can provide users with an interface to access and communicate with the main server system 1602, and to utilize the functional aspects of the system. The user access points 1634 can comprise a user interface to display images to the user and to allow users to enter commands. The user access points 1634 can comprise user data that can be stored with the user profile.

Computer System

Figure 17:
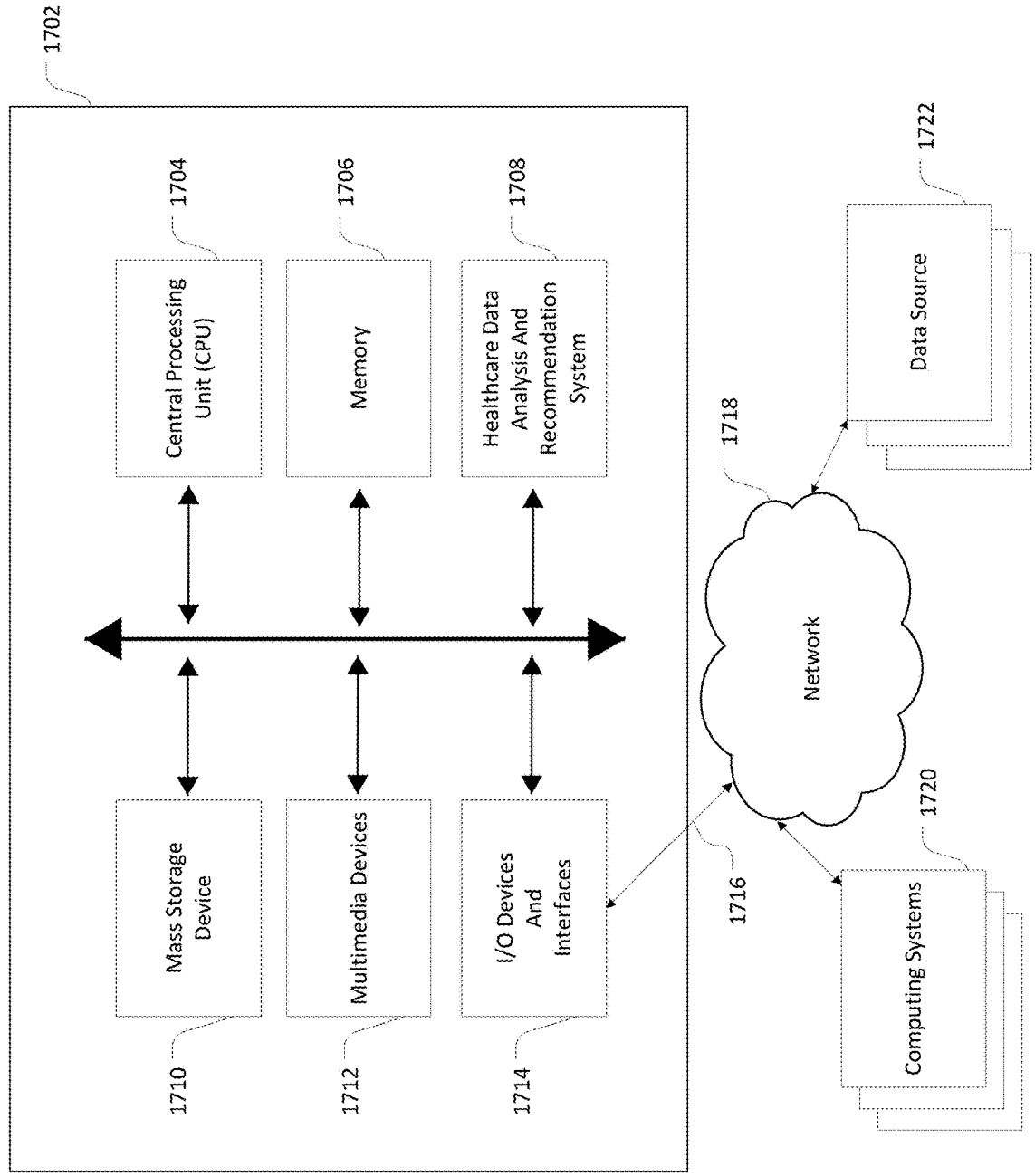
FIG. 17 illustrates a block diagram depicting an example embodiment of a computer hardware system configured to run software for implementing one or more embodiments of the systems described herein.

In some embodiments, the systems, processes, and methods described herein are implemented using a computing system, such as the one illustrated in FIG. 17. The example computer system 1702 is in communication with one or more computing systems 1720 and/or one or more data sources 1722 via one or more networks 1718. In addition, in some embodiments, the computer system 1702 may be configured to manage access or administer a software application as described herein. While FIG. 17 illustrates an embodiment of a computer system 1702, it is recognized that the functionality provided for in the components and modules of computer system 1702 can be combined into fewer components and modules, or further separated into additional components and modules.

Computing System Components

The computer system 1702 can comprise a healthcare data analysis and recommendation system 1708 that carries out the functions, methods, acts, and/or processes described herein. The computer system 1702 can comprise a healthcare data analysis and recommendation system 1708 that is executed on the computer system 1702 by a central processing unit 1704 discussed further below.

In general the word "module," as used herein, refers to logic embodied in hardware or firmware or to a collection of software instructions, having entry and exit points. Modules are written in a program language, such as JAVA, C, or C++, JSON, HTML, Java Script or the like. Software modules can be compiled or linked into an executable program, installed in a dynamic link library, or can be written in an interpreted language such as BASIC, PERL, LAU, PHP or Python and any such languages. Software modules can be called from other modules or from themselves, and/or can be invoked in response to detected events or interruptions. Modules implemented in hardware include connected logic units such as gates and flip-flops, and/or can comprise programmable units, such as programmable gate arrays or processors.

Generally, the modules described herein refer to logical modules that can be combined with other modules or divided into sub-modules despite their physical organization or storage. The modules are executed by one or more computing systems, and can be stored on or within any suitable computer readable medium, or implemented in-whole or in-part within special designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The computer system 1702 includes one or more processing units (CPU) 1704, which can comprise a microprocessor. The computer system 1702 further includes a physical memory 1706, such as random access memory (RAM) for temporary storage of information, a read only memory (ROM) for permanent storage of information, and a mass storage device 1710, such as a backing store, hard drive, rotating magnetic disks, solid state disks (SSD), flash memory, phase-change memory (PCM), 3D XPoint memory, diskette, or optical media storage device. Alternatively, the mass storage device can be implemented in an array of servers. Typically, the components of the computer system 1702 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1702 includes one or more input/output (I/O) devices and interfaces 1714, such as a keyboard, mouse, touch pad, and printer. The I/O devices and interfaces 1714 can comprise one or more display devices, such as a monitor, that allows the visual presentation of data to a user. More particularly, a display device provides for the presentation of GUIs as application software data, and multi-media presentations, for example. The I/O devices and interfaces 1714 can also provide a communications interface to various external devices. The computer system 1702 can comprise one or more multi-media devices 1712, such as speakers, video cards, graphics accelerators, and microphones, for example.

Computing System Device/Operating System

FIG. 17 is a block diagram depicting an embodiment of a computer hardware system configured to run software for implementing one or more embodiments of a healthcare data analysis and recommendation system.

The computer system 1702 can run on a variety of computing devices, such as a server, a Windows server, a Structure Query Language server, a UNIX server, a personal computer, a mainframe computer, a laptop computer, a tablet computer, a cell phone, a smartphone, a personal digital assistant, a kiosk, an audio player, an e-reader device, and so forth. In other embodiments, the computer system 1702 can run on a cluster computer system, a mainframe computer system and/or other computing system suitable for controlling and/or communicating with large databases, performing high volume transaction processing, and generating reports from large databases. The computing system 1702 is generally controlled and coordinated by operating system software, such as z/OS, Windows, Linux, UNIX, BSD, PHP, SunOS, Solaris, MacOS, ICloud services or other compatible operating systems, including proprietary operating systems. Operating systems control and schedule computer processes for execution, perform memory management, provide file system, networking, and I/O services, and provide a user interface, such as a graphical user interface (GUI), among other things.

Network

The computer system 1702 illustrated in FIG. 17 is coupled to a network 1718, such as a LAN, WAN, or the Internet via a communication link 1716 (wired, wireless, or a combination thereof). Network 1718 communicates with various computing devices and/or other electronic devices. Network 1718 is communicating with one or more computing systems 1720 and one or more data sources 1722. The computer system 1702 can comprise a healthcare data analysis and recommendation system 1708 can access or can be accessed by computing systems 1720 and/or data sources 1722 through a web-enabled user access point. Connections can be a direct physical connection, a virtual connection, and other connection type. The web-enabled user access point can comprise a browser module that uses text, graphics, audio, video, and other media to present data and to allow interaction with data via the network 1718.

The output module can be implemented as a combination of an all-points addressable display such as a cathode ray tube (CRT), a liquid crystal display (LCD), a plasma display, or other types and/or combinations of displays. The output module can be implemented to communicate with input devices and/or interfaces 1714 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module can communicate with a set of input and output devices to receive signals from the user.

Other Systems

In addition to the systems that are illustrated in FIG. 17, the network 1718 may communicate with other data sources or other computing devices. The computing system 1702 can comprise one or more internal and/or external data sources (for example, data sources 1722). In some embodiments, one or more of the data repositories and the data sources described above can be implemented using a relational database, such as DB2, Sybase, Oracle, CodeBase, and Microsoft® SQL Server as well as other types of databases such as a flat-file database, an entity relationship database, and object-oriented database, record-based database, and/or a graphical database such as Neo4J.

The computer system 1702 can also access one or more data sources 1722. The data sources 1722 can be stored in a database or data repository. The computer system 1702 can access the one or more data sources 1722 through a network 1718 or can directly access the database or data repository through I/O devices and interfaces 1714. The data repository storing the one or more data sources 1722 can reside within the computer system 1702.

URLs and Cookies

In some embodiments, one or more features of the systems, methods, and devices described herein can utilize a URL and/or cookies, for example for storing and/or transmitting data or user information. A Uniform Resource Locator (URL) can comprise a web address and/or a reference to a web resource that is stored on a database and/or a server. The URL can specify the location of the resource on a computer and/or a computer network. The URL can comprise a mechanism to retrieve the network resource. The source of the network resource can receive a URL, identify the location of the web resource, and transmit the web resource back to the requestor. A URL can be converted to an IP address, and a Doman Name System (DNS) can look up the URL and its corresponding IP address. URLs can be references to web pages, file transfers, emails, database accesses, and other applications. The URLs can comprise a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can comprise data sent from a website and/or stored on a user's computer. This data can be stored by a user's web browser while the user is browsing. The cookies can comprise useful information for websites to remember prior browsing information, such as a shopping cart on an online store, clicking of buttons, login information, and/or records of web pages or network resources visited in the past. Cookies can also comprise information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Browser Module and Input Devices

The browser module may be implemented as a combination of an all points addressable display such as a cathode-ray tube (CRT), a liquid crystal display (LCD), a plasma display, or other types and/or combinations of displays. In addition, the browser module may be implemented to communicate with input/output devices 1714 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

Data Sources

In some embodiments, the system 1702 may comprise a physical or logical connection established between a remote microprocessor and a mainframe host computer for the express purpose of uploading, downloading, or viewing interactive data and databases on-line in real time. The remote microprocessor may be operated by an entity operating the computer system 1702, including the client server systems or the main server system, an/or may be operated by one or more of the data sources 1722 and/or one or more of the computing systems 1720. In some embodiments, terminal emulation software may be used on the microprocessor for participating in the micro-mainframe link.

In some embodiments, computing systems 1720 who are internal to an entity operating the computer system 1702 may access the healthcare data analysis and recommendation system module 1708 internally as an application or process run by the CPU 1704.

User Access Point

In an embodiment, a user access point or user interface comprises a personal computer, a laptop computer, a tablet computer, an e-reader device, a cellular phone, a smartphone, a GPS system, a Blackberry® device, a portable computing device, a server, a computer workstation, a local area network of individual computers, an interactive kiosk, a personal digital assistant, an interactive wireless communications device, a handheld computer, an embedded computing device, an audio player, or the like.

Appendix A

Appendix A comprises various charts including, for example data definitions. Pages 1-12 comprise a chart, titled "p3 Data Input Variables", of example input variables that may be used by the processing engine and/or reporting engine to determine risk levels, conditions, and/or treatment recommendations, and to generate patient reports according to various embodiments herein. The chart comprises variable names, variable categories (e.g. basic labs, advanced labs, biometrics, etc.), variable descriptions, and example functions/formulas/algorithms. Pages 13-16 comprise a chart, titled "p3 Lab & Diagnostic Functions," of example lab and diagnostic functions for calculating various health parameters for use in the system according to various embodiments herein. The chart comprises descriptions, function names, categories, example algorithms, and example calculations. Pages 17-20 comprise a chart, titled "p3 Condition Functions," of example condition determination functions. The chart comprises condition names, function names, categories, example algorithms, and example threshold levels. Pages 21-32 comprise a chart, titled "p3 Risk Functions," of example risk determination functions according to various embodiments herein. The chart comprises descriptions, names, categories, example algorithms, risk descriptions, and example risk levels. Pages 33-34 comprise a chart, titled "p3 Score Functions," of example score functions for calculating various health-related scores, including Lifestyle Scores, according to various embodiments herein. Pages 35-39 comprise a chart, titled "p3 Medication Treatment Functions," of example medication treatment recommendation functions according to various embodiments herein. The chart comprises descriptions, function names, categories, example algorithms, example treatments, and example treatment recommendation decision functions. Pages 40-42 comprise a chart, titled "p3 Lifestyle Treatment Functions," of example lifestyle treatment recommendation functions according to various embodiments herein. The chart comprises descriptions, function names, categories, example algorithms, example treatments, and example treatment recommendation decision functions. Pages 43-50 comprise a chart, titled "p3 Testing Treatment Functions," of example treatment and/or medical testing recommendation functions according to various embodiments herein. The chart comprises descriptions, function names, example algorithms, and example testing recommendations. The input variables and functions that can be utilized according to the embodiments herein are not limited to the example input variables and functions of Appendix A.

Alternative Embodiments

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. For example, while the embodiments herein have been disclosed in the context of treatment of heart attack, stroke, and diabetes, it will be understood that they may be applied to any health condition. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments can be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or blocks. Thus, such conditional language is not generally intended to imply that features, elements and/or blocks are in any way required for one or more embodiments or that one or more embodiments necessarily include logic for deciding, with or without user input or prompting, whether these features, elements and/or blocks are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (for example, as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (for example, as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

What is claimed is:

1. A system for personalized medical risk identification and generation of a dynamic personalized patient health reporting interface, the system comprising:

a processing engine configured to interface with a plurality of medical data sources, wherein at least one medical data source of the plurality of medical data sources comprises medical data having an incongruent data structure to another medical data source of the plurality of medical data sources, wherein at least one medical data source of the plurality of medical data sources comprises an electronically accessible patient survey interface, wherein the patient survey interface is accessible via input of a unique activation code generated by the system, and wherein the medical data comprises one or more medical data types;

a reporting engine configured to generate the dynamic personalized patient health reporting interface and update the dynamic personalized patient health reporting interface in response to a medical provider or specific patient input;

a system update interface configured to enable the medical provider to input data for new system logic, or for updates to existing system logic, for use by the processing engine in medical risk identification, the system update interface comprising:

a function type menu for the medical provider to select a function type from a plurality of function types, wherein the plurality of function types comprise functions that apply a combination of if-then statements to patient data for medical risk identification;

one or more patient data type menus for the medical provider to select a patient data type for use in one or more if-then statements of the selected function type; and one or more data range menus for the medical provider to define data ranges corresponding to the selected patient data type;

one or more computer readable storage devices configured to store a plurality of computer executable instructions; and one or more hardware computer processors in communication with the one or more computer readable storage devices and configured to execute the plurality of computer executable instructions in order to cause the system to:

collect and aggregate medical data for a specific patient from one or more of the plurality of medical data sources including at least the electronically accessible patient survey interface and at least one other medical data source;

perform, by the processing engine, an adaptive rule-based analysis of the aggregated medical data for the specific patient to identify a patient medical risk level for the specific patient, wherein the rule-based analysis comprises both collectively and individually evaluating each medical data type of the aggregated medical data, and wherein the rule-based analysis comprises applying, to the medical data for the specific patient, one or more functions comprising a combination of if-then statements inputted to the system update interface;

develop, by the processing engine, one or more patient treatment recommendations and/or treatment regimens for the specific patient based on the identified patient medical risk level;

generate, by the reporting engine, the dynamic patient health reporting interface comprising a visual representation of the patient medical risk level and/or the one or more patient treatment recommendations and/or treatment regimens for the specific patient;

display, to the medical provider, the dynamic patient health reporting interface, wherein the dynamic patient health reporting interface comprises one or more first interactive elements, the one or more first interactive elements comprising at least a modification mechanism, wherein the modification mechanism can be activated by the medical provider to adjust the patient treatment recommendations and/or treatment regimens; and display, to the specific patient, the dynamic patient health reporting interface, wherein the dynamic patient health reporting interface comprises one or more second interactive elements for interaction with by the specific patient.

2. The system of claim 1, wherein the one or more first interactive elements comprise at least an approval mechanism, wherein the approval mechanism can be activated by the medical provider to select one or more patient treatment recommendations and/or treatment regimens for the specific patient.

3. The system of claim 2, wherein the reporting engine is further configured to programmatically generate and display, through the dynamic patient health reporting interface, a patient education plan upon activation of the approval mechanism.

4. The system of claim 1, further comprising a data entry user interface configured to allow the medical provider to input the medical data into the system.

5. The system of claim 4, wherein the data entry user interface is further configured to update through utilization of an application programming interface.

6. The system of claim 4, wherein the data entry user interface is further configured to update through importation of medical data from a .CSV, .DOC, and/or .XLS file.

7. The system of claim 1, wherein the function type menu, the one or more patient data type menus, and the one or more data range menus each comprise drop-down menus.

8. The system of claim 1, wherein identifying the patient medical risk level comprises making at least one individual or aggregated lab, diagnostic, and/or biometric risk determination.

9. The system of claim 1, wherein identifying the patient medical risk level comprises calculating at least one risk calculation formula score.

10. The system of claim 1, wherein the one or more patient treatment recommendations and/or treatment regimens comprise at least one of sodium restrictions, specific food/drink recommendations, cardiovascular exercise, high intensity interval training (HIIT), strength training, flexibility training, weight lifting regimens, stress relief, sleep regimens, body composition improvement, quitting tobacco or assisting with other drug dependence, addiction rehabilitation, reduction of high cholesterol, high and/or low blood pressure treatment, recovery from heart attack and/or stroke, prevention of congestive heart failure, heart disease prevention, allergy treatment, prevention of cerebrovascular and/or cardiovascular disease, diabetes treatment, antithrombotic treatments, metabolism improvement, niacin deficiency treatment, treatment of sleep apnea and other sleep disorders, or uric acid disorders.

11. The system of claim 1, wherein the medical data comprises one or more of lipid profile data, low-density lipoprotein, triglycerides, lipoprotein a, small dense LDL, cholesterol particle measurements, inflammation lab profile data, Oxidized low-density lipoprotein, ADMA, SDMA, Urinary Microalbumin/Creatinine Ratio, High-Sensitive C-Reactive Protein (hsCRP), Lipoprotein-associated phospholipase-A2, Lipoprotein-associated phospholipase-A2 Activity, Myeloperoxidase, microbiome labs, insulin resistance and diabetes laboratory tests, GlycoMark, Insulin Sensitivity, Homeostatic Model Assessment for Insulin Resistance, Beta Cell Function, Oral Glucose Tolerance Testing, myocardial laboratory tests markers, N-Terminal proBNP, SMC Cardiac Troponin, platelet function tests, vitamin and supplement labs, diagnostic data, Endothelial Function test, Ankle-brachial Pressure Index, Calcium Artery Score, Abdominal Aortic Aneurysm Screening, Echocardiogram, OralDNA/MyPeriopath, Obstructive Sleep Apnea test, biometric data, patient history, or lifestyle habits.

12. The system of claim 1, wherein the patient medical risk level comprises clinical risk identification for at least one of heart attack, stroke and diabetes.

13. The system of claim 1, wherein the dynamic patient health reporting interface further comprises one or more medication, treatment, preventative, health, lifestyle, or behavioral recommendations.

14. The system of claim 1, further comprising a report approval interface configured to allow the medical provider to approve, modify, and/or reject the generated dynamic patient health reporting interface.

15. The system of claim 1, wherein at least one of the plurality of medical data sources comprises an electronic health record (EHR).

16. The system of claim 1, wherein identifying the patient medical risk level comprises:
 calculating the specific patient Carotid Intima-Media Thickness (CIMT) percentile, wherein calculating the specific patient CIMT percentile comprises:
  obtaining values for parameters $\gamma_0$ and $\gamma_1$ for each of patient ages 40-70 by solving a non-linear equation of the form percentile $_{(age-level)}=1/1+\exp(-(\gamma_0+\gamma_1 CIMT))$ using beta regression; and
  estimating, using the non-linear equation and obtained values for parameters $\gamma_0$ and $\gamma_1$, a patient CIMT percentile for the specific patient.

17. The system of claim 16, wherein identifying the patient medical risk level comprises:
 calculating the specific patient Carotid Intima-Media Thickness (CIMT) age, wherein calculating the patient CIMT age comprises:
  obtaining values for parameters $\delta_0$ and $\delta_1$ by solving a linear equation of the form age=$\delta_0+\delta_1 CIMT$ using the $50^{th}$ percentile CIMT across patients aged 40-70; and
  calculating the patient CIMT age using the linear equation and the obtained values for parameters $\delta_0$ and $\delta_1$.

18. The system of claim 1, wherein the one or more medical data types comprise at least the following: diagnostic data, historic population data, historic patient data, lab testing data, medication data, lifestyle data, biographical data, and medical imaging data.

19. A system for personalized medical risk identification and generation of a dynamic personalized patient health reporting interface, the system comprising:
 a processing engine configured to interface with a plurality of medical data sources, wherein at least one medical data source of the plurality of medical data sources comprises medical data having an incongruent data structure to another medical data source of the plurality of medical data sources, wherein at least one medical data source of the plurality of medical data sources comprises an electronically accessible patient survey interface, wherein the patient survey interface is accessible via input of a unique activation code generated by the system, and wherein the medical data comprises one or more medical data types;
 a reporting engine configured to generate the dynamic personalized patient health reporting interface and update the dynamic personalized patient health reporting interface in response to a medical provider or specific patient input;
 a system update interface configured to enable the medical provider to input data for new system logic, or for updates to existing system logic, for use by the processing engine in medical risk identification, the system update interface comprising:
- a function type menu for the medical provider to select a function type from a plurality of function types, wherein the plurality of function types comprise functions that apply a combination of if-then statements to patient data for medical risk identification;
- one or more patient data type menus for the medical provider to select a patient data type for use in one or more if-then statements of the selected function type; and
- one or more data range menus for the medical provider to define data ranges corresponding to the selected patient data type;

one or more computer readable storage devices configured to store a plurality of computer executable instructions; and one or more hardware computer processors in communication with the one or more computer readable storage devices and configured to execute the plurality of computer executable instructions in order to cause the system to:
- collect and aggregate medical data for a specific patient from one or more of the plurality of medical data sources including at least the electronically accessible patient survey interface and at least one other medical data source;
- perform, by the processing engine, an adaptive rule-based analysis of the aggregated medical data for the specific patient to identify a patient medical risk level for the specific patient, wherein the rule-based analysis comprises both collectively and individually evaluating each medical data type of the aggregated medical data, and wherein the rule-based analysis comprises applying, to the medical data for the specific patient, one or more functions comprising a combination of if-then statements inputted to the system update interface;
- develop, by the processing engine, one or more patient treatment recommendations and/or treatment regimens for the specific patient based on the identified patient medical risk level;
- generate, by the reporting engine, the dynamic patient health reporting interface comprising a visual representation of the patient medical risk level and/or the one or more patient treatment recommendations and/or treatment regimens for the specific patient;
- display, to the medical provider, the dynamic patient health reporting interface, wherein the dynamic patient health reporting interface comprises one or more first interactive elements, wherein the one or more first interactive elements comprise at least an approval mechanism, wherein the approval mechanism can be activated by the medical provider to select one or more patient treatment recommendations and/or treatment regimens for the specific patient, and wherein the reporting engine is further configured to programmatically generate and display, through the dynamic patient health reporting interface, a patient education plan upon activation of the approval mechanism; and
- display, to the specific patient, the dynamic patient health reporting interface, wherein the dynamic patient health reporting interface comprises one or more second interactive elements for interaction with by the specific patient.

20. A system for personalized medical risk identification and generation of a dynamic personalized patient health reporting interface, the system comprising:
- a processing engine configured to interface with a plurality of medical data sources, wherein at least one medical data source of the plurality of medical data sources comprises medical data having an incongruent data structure to another medical data source of the plurality of medical data sources, wherein at least one medical data source of the plurality of medical data sources comprises an electronically accessible patient survey interface, wherein the patient survey interface is accessible via input of a unique activation code generated by the system, and wherein the medical data comprises one or more medical data types;
- a reporting engine configured to generate the dynamic personalized patient health reporting interface and update the dynamic personalized patient health reporting interface in response to a medical provider or specific patient input;
- a system update interface configured to enable the medical provider to input data for new system logic, or for updates to existing system logic, for use by the processing engine in medical risk identification, the system update interface comprising:
  - a function type menu for the medical provider to select a function type from a plurality of function types, wherein the plurality of function types comprise functions that apply a combination of if-then statements to patient data for medical risk identification;
  - one or more patient data type menus for the medical provider to select a patient data type for use in one or more if-then statements of the selected function type; and
  - one or more data range menus for the medical provider to define data ranges corresponding to the selected patient data type;
- one or more computer readable storage devices configured to store a plurality of computer executable instructions; and
- one or more hardware computer processors in communication with the one or more computer readable storage devices and configured to execute the plurality of computer executable instructions in order to cause the system to:
  - collect and aggregate medical data for a specific patient from one or more of the plurality of medical data sources including at least the electronically accessible patient survey interface and at least one other medical data source;
  - perform, by the processing engine, an adaptive rule-based analysis of the aggregated medical data for the specific patient to identify a patient medical risk level for the specific patient, wherein the rule-based analysis comprises both collectively and individually evaluating each medical data type of the aggregated medical data, and wherein the rule-based analysis comprises applying, to the medical data for the specific patient, one or more functions comprising a combination of if-then statements inputted to the system update interface,
  - wherein identifying the patient medical risk level comprises:
    - calculating the specific patient Carotid Intima-Media Thickness (CIMT) percentile, wherein calculating the specific patient CIMT percentile comprises:

obtaining values for parameters $\gamma 0$ and $\gamma 1$ for each of patient ages 40-70 by solving a non-linear equation of the form percentile (age-level)=1/1+exp(−($\gamma 0$+$\gamma 1$CIMT)) using beta regression; and estimating, using the non-linear equation and obtained values for parameters $\gamma 0$ and $\gamma 1$, a patient CIMT percentile for the specific patient; and calculating the specific patient Carotid Intima-Media Thickness (CIMT) age, wherein calculating the patient CIMT age comprises:

obtaining values for parameters $\delta 0l$ and $\delta 1$ by solving a linear equation of the form age=$\delta 0$+$\delta 1$CIMT using the 50th percentile CIMT across patients aged 40-70; and calculating the patient CIMT age using the linear equation and the obtained values for parameters $\delta 0l$ and $\delta 1$;

develop, by the processing engine, one or more patient treatment recommendations and/or treatment regimens for the specific patient based on the identified patient medical risk level;

generate, by the reporting engine, the dynamic patient health reporting interface comprising a visual representation of the patient medical risk level and/or the one or more patient treatment recommendations and/or treatment regimens for the specific patient; and display, to the specific patient, the dynamic patient health reporting interface, wherein the dynamic patient health reporting interface comprises one or more interactive elements.

* * * * *